United States Patent
Watanabe et al.

(10) Patent No.: US 11,370,741 B2
(45) Date of Patent: Jun. 28, 2022

(54) PROCESSES FOR PREPARING ALPHA-NECRODYL COMPOUNDS AND PROCESSES FOR PREPARING GAMMA-NECRODYL COMPOUNDS

(71) Applicant: Shin-Etsu Chemical Co., Ltd., Tokyo (JP)

(72) Inventors: Tomohiro Watanabe, Niigata (JP); Takeshi Kinsho, Niigata (JP); Yusuke Nagae, Niigata (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 0 days.

(21) Appl. No.: 17/378,952

(22) Filed: Jul. 19, 2021

(65) Prior Publication Data

US 2022/0024847 A1     Jan. 27, 2022

(30) Foreign Application Priority Data

Jul. 22, 2020 (JP) .............................. JP2020-125808

(51) Int. Cl.
*C07C 67/293* (2006.01)
*C07C 67/327* (2006.01)

(52) U.S. Cl.
CPC .......... *C07C 67/327* (2013.01); *C07C 67/293* (2013.01)

(58) Field of Classification Search
None
See application file for complete search history.

(56) References Cited

U.S. PATENT DOCUMENTS

2021/0206711 A1 * 7/2021 Chebny ................... C07C 67/48

OTHER PUBLICATIONS

Richers et al. "Synthesis and Neurotrophic Activity Studies of Illicium Sesquiterpene Natural Product Analogues" Chemistry A European Journal, 23:3178-3183 (2017).
Figadére et al. "trans-a-Necrodyl isobutyrate, the sex pheromone of the grape mealybug, Pseudococcus maritimus" Tetrahedron Letters, 48:8434-8437 (2007).
Franco et al. "Novel Approaches for the Management of Mealybug Pests" Biorational Control of Arthropod Pests, 233-278 (2009).
Jacobs et al. "Defense mechanisms of arthropods. 84. Synthesis of (−)-α-necrodol and (−)-β-necrodol: Novel cyclopentanoid terpenes from a carrion beetle" Journal of Organic Chemistry, 55:4051-4062 (1990).
Levi-Zada et al. "Identification of the Sex Pheromone of the Spherical Mealybug Nipaecoccus viridi" Journal of Chemical Ecology, 45:455-463 (2019).
Millar et al. "Chemistry and Applications of Mealybug Sex Pheromones" Semiochemicals in Pest and Weed Control, Chapter 2, pp. 11-27 (2005).
Ross et al. "Scale insects" Current Biology, 19(5):R184-R186 (2009).
Tabata et al. "Sex pheromone of a coccoid insect with sexual and asexual lineages: fate of an ancestrally essential sexual signal in parthenogenetic females" Journal of the Royal Society Interface, 14:1-11 (2017).
Tabata et al. "Sexual attractiveness and reproductive performance in ageing females of a coccoid insect" Biology Letters, 14:1-5 (2018).
Zou et al. "Chemistry of the pheromones of mealybug and scale insects" Natural Product Reports, 32:1067-1113 (2015).
Zou et al. "Synthesis and Bioassay of Racemic and Chiral trans-alpha-Necrodyl Isobutyrate, the Sex Pheromone of the Grape Mealybug Pseudococcus maritimus" Journal of Agricultural and Food Chemistry, 58:4977-4982 (2010).

(Continued)

*Primary Examiner* — Amy C Bonaparte
(74) *Attorney, Agent, or Firm* — Myers Bigel, P.A.

(57) ABSTRACT

The present invention provides processes for preparing an α-necrodyl compound of the following general formula (3): wherein $R^2$ represents a monovalent hydrocarbon group having 1 to 9 carbon atoms, the process comprising: subjecting a 3, 5, 5-trimethyl-3-cyclopentene compound of the following general formula (1): wherein $R^2$ is as defined above, and X represents a leaving group, to a nucleophilic substitution reaction with a methylating agent of the following general formula (2): wherein M represents Li, $MgZ^1$, $ZnZ^1$, Cu, $CuZ^1$, or $CuLiZ^1$, and $Z^1$ represents a halogen atom or a methyl group, to form the α-necrodyl compound (3). The present invention further provides processes for preparing γ-necrodyl compounds of the following general formula (4): wherein $R^2$ represents a monovalent hydrocarbon group having 1 to 9 carbon atoms, the process comprising: subjecting the α-necrodyl compound (3) thus obtained to a positional isomerization reaction at the double bond to form the γ-necrodyl compound (4).

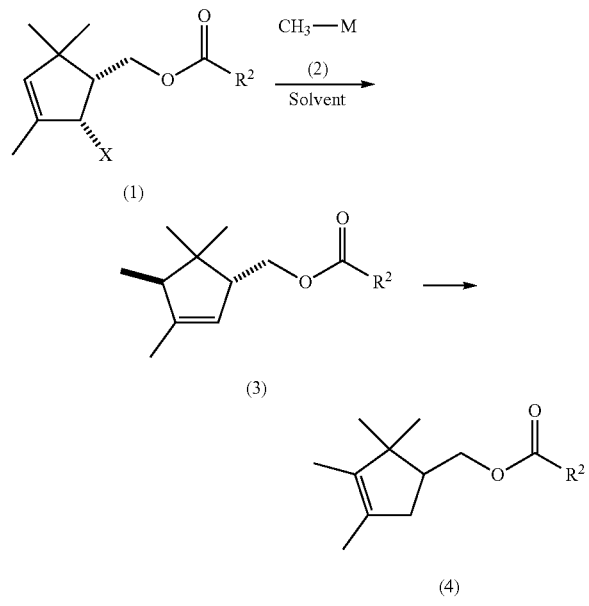

11 Claims, No Drawings

(56) References Cited

OTHER PUBLICATIONS

Cocker et al. "The chemistry of terpenes. Part XVII. Synthesis of (+)-cis-homocaronic acid (cis-3-carboxymethyl-2,2-dimethylcyclopropanecarboxylic acid) and some related compounds" J. Chemical Soc, pp. 194-202 (1974).

Crowley et al. "Photoisomerizations. X. The Photochemical Transformations of Alloocimene" The Journal of Organic Chemistry, 33(10):3679-3686 (1968).

Huisgen et al. "Cycloadditions to Methyl 3,3-Dimethyl-3H-pyrazole-5-carboxylate" Journal of the Chemical Society, Chemical Communications, pp. 568-570 (1979).

\* cited by examiner

PROCESSES FOR PREPARING ALPHA-NECRODYL COMPOUNDS AND PROCESSES FOR PREPARING GAMMA-NECRODYL COMPOUNDS

TECHNICAL FIELD

The present invention relates to processes for preparing α-necrodyl compounds and processes for preparing γ-necrodyl compounds. The present invention relates also to processes for preparing α-necrodyl compounds and processes for preparing γ-necrodyl compounds, both starting from a novel compound, (1RS,2SR)-(2-hydroxy-3,5,5-trimethyl-3-cyclopentenyl)methanol. The present invention relates further to a novel compound, (2-hydroxy-3,5,5-trimethyl-3-cyclopentenyl)methanol.

BACKGROUND ART

An α-necrodyl compound, or a group of compounds having a (3,4,5,5-tetramethyl-2-cyclopentenyl)methyl group, and a γ-necrodyl compound, or a group of compounds having a (2,2,3,4-tetramethyl-3-cyclopentenyl) methyl group, are often seen in natural products such as pheromones which are biologically active substances. For instance, a kind of α-necrodyl compound, α-necrodol, is known as a defensive substance of red-lined carrion beetle (scientific name: *Necrodes surinamensis*) (Non-Patent Literature 1 listed below). Another kind of α-necrodyl compound, α-necrodyl isobutyrate, was identified as a sex pheromone of grape mealybug (scientific name: *Pseudococcus maritimus*) (Non-Patent Literatures 2 and 3 listed below). A kind of γ-necrodyl compound, γ-necrodyl isobutyrate, was also identified as a sex pheromone of spherical mealybug (scientific name: *Nipaecoccus viridis*) (Non-Patent Literature 4 listed below).

Sex pheromones of insects are biologically active substances which usually have a function for female to attract male. Even a small amount of them exhibits high attracting activity. Many applications for managing pests with the sex pheromones have been devised and practiced. For instance, the sex pheromones are widely used as a means of forecasting outbreak of pests and confirming geographic spread (invasion into a specific area), and as a means of controlling pests. Widely used methods of controlling pests are a mass trapping method, a lure and kill or attract and kill method, a lure and infect or attract and infect method, and a mating disruption method. Trapping with a sex pheromone exhibits high attracting ability and species-specific and, therefore, is very useful for detecting and monitoring pests of interest.

Mealybugs are small insects which suck plant sap. Some species of them seriously damage grains and fruit plants and are agriculturally key noxious insects. Mealybugs live on plant tissues such as knots or remains of flower parts, and therefore, are often difficult to find. Accordingly, it is difficult to remove mealybugs in plant quarantine for crops. Thus, sex pheromone-based traps are useful means for controlling mealybugs.

Adult female mealybugs lack wings, have degenerated legs, and accordingly, transfer only a little. Adult male mealybugs have wings, are tiny and fragile, eat nothing after eclosion, and survive for a maximum of several days (Non-Patent Literatures 5 and 6 listed below). Sex pheromone released from such sessile females, which is essential to attract such ephemeral males, plays a key role in finding a mating partner. The sex pheromone is believed to be under high selective pressure in evolution (Non-Patent Literatures 7 and 8). In fact, pheromones of mealybugs have a wide variety of highly species-specific structures (Non-Patent Literatures 9 and 10 listed below). Therefore, sex pheromones of mealybugs are useful means for pest control and pest quarantine and also are important models for studying variation of chemical communication mechanisms of insects.

LIST OF THE PRIOR ART

[Non-Patent Literature 1] J. Meinwald et al., J. Org. Chem., 1990, 55, 4051-4062.
[Non-Patent Literature 2] J. G. Millar et al., Tetrahedron Lett., 2007, 48, 8434-8437.
[Non-Patent Literature 3] J. G. Millar et al., J. Agric. Food Chem., 2010, 58, 4977-4982.
[Non-Patent Literature 4] A. Levi-Zada et al., J. Chem. Ecol., 2019, 45, 455-463.
[Non-Patent Literature 5] J. C. Franco et al., Biorational Control of Arthropod Pests; I. Ishaaya, A. R. Horowitz, Eds., Springer, Dordrecht, 2009, 233-278.
[Non-Patent Literature 6] L. Ross et al., Curr. Biol., 2009, 19, R184-R186.
[Non-Patent Literature 7] J. Tabata et al., J. R. Soc. Interface, 2017, 14, 20170027.
[Non-Patent Literature 8] J. Tabata et al., Biol. Lett., 2018, 14, 20190262.
[Non-Patent Literature 9] J. G. Millar et al., Semiochemicals in Pest and Weed Control, 2005, Chapter 2, 11-27.
[Non-Patent Literature 10] J. G. Millar et al., Nat. Prod. Rep., 2015, 32, 1067.

SUMMARY OF THE INVENTION

Processes for synthesizing α-necrodyl compounds are known, as described in Meinwald et al., Non-Patent Literature 1, and in Millar et al., Non-Patent Literature 3. A process for synthesizing γ-necrodyl compounds is known, as described in Levi-Zada, Non-Patent Literature 4.

However, the process described in Non-Patent Literature 1 is not suitable to the preparation in an industrial scale, because the process requires expensive reagents such as ruthenium oxide, t-butyldimethylchlorosilane, phenylselenenyl chloride, and a sulfur trioxide-pyridine complex, and an explosive reagent such as diazomethane, a reaction using liquid ammonia, which is difficult to perform in a usual reaction equipment, and purification of an intermediate by preparative HPLC. The preparation process is less efficient, because it comprises as many as 13 steps to prepare α-necrodol from a starting material camphoric anhydride.

The process described in Non-Patent Literature 3 is not suitable to the preparation in an industrial scale, because sodium hydride is used in an intramolecular Knoevenagel reaction. Dimethyl zinc, which ignites easily in air, is used in a step of introducing a methyl group into an α,β-unsaturated ketone by a conjugate addition reaction; and hexamethylphosphoric triamide, which is highly toxic, is used in methylation. Metallic lithium in ethylenediamine is used in a step of isomerizing an exo-olefin into a tri-substituted olefin. This reaction is difficult to stop at a proper timing. If this reaction continues for a too long period of time, undesired tetra-substituted olefin forms which may decrease the yield. Moreover, these compounds are difficult to separate. The series of synthesis comprises 8 steps, starting from methyl acetoacetate, resulting in a yield of 7%. Thus, the process is inefficient.

In the process described in Non-Patent Literature 4, α-necrodyl acetate is obtained by distillation purification of an essential oil of *Lavandula luisieri*, and the ester is subjected to solvolysis, followed by isomerization of the double bond using boron trifluoride-ethyl ether complex, and acylation of alcohol to obtain γ-necrodyl isobutyrate. It is difficult to separate compounds having similar properties in a method of obtaining a starting material from a natural essential oil, so that a final product may be contaminated with impurities. Therefore, such method is inappropriate for synthesizing a biologically active substance which exhibits an activity in a trace amount.

The present invention has been made in these circumstances, and aims to provide processes for preparing α-necrodyl compounds and processes for preparing γ-necrodyl compounds, efficiently.

As a result of the intensive researches, the present inventors have found that an α-necrodyl compound is prepared by a nucleophilic substitution reaction of a 3,5,5-trimethyl-3-cyclopentene compound, and thus have completed the present invention. The present inventors also have found that a γ-necrodyl compound is prepared by a positional isomerization at a double bond of an α-necrodyl compound, and thus have completed the present invention.

According to one aspect of the present invention, the present invention provides a process for preparing an α-necrodyl compound of the following general formula (3):

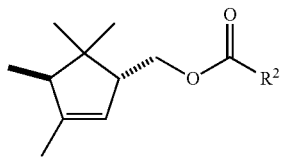

(3)

wherein $R^2$ represents a monovalent hydrocarbon group having 1 to 9 carbon atoms, and a bold unwedged bond and a hashed unwedged bond represent a relative configuration, the process comprising:
  subjecting a 3, 5, 5-trimethyl-3-cyclopentene compound of the following general formula (1):

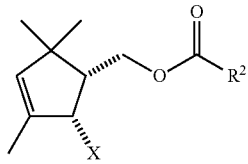

(1)

wherein $R^2$ is as defined above, X represents a leaving group, and hashed unwedged bonds represent a relative configuration, to a nucleophilic substitution reaction with a methylating agent of the following general formula (2):

CH$_3$-M  (2)

wherein M represents Li, MgZ$^1$, ZnZ$^1$, Cu, CuZ$^1$, or CuLiZ$^1$, and Z$^1$ represents a halogen atom or a methyl group, to form the α-necrodyl compound (3).

According to another aspect of the present invention, the present invention provides a process for preparing a γ-necrodyl compound of the following general formula (4):

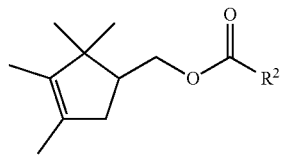

(4)

wherein $R^2$ represents a monovalent hydrocarbon group having 1 to 9 carbon atoms, the process comprising:
  the aforesaid process for preparing the α-necrodyl compound (3), and
  subjecting the α-necrodyl compound (3) thus obtained to a positional isomerization reaction at the double bond to form the γ-necrodyl compound (4).

According to another aspect of the present invention, the present invention provides a process for preparing the α-necrodyl compound (3), the process comprising:
  subjecting (1RS,2SR)-(2-hydroxy-3, 5, 5-trimethyl-3-cyclopentenyl)methanol of the following formula (5C):

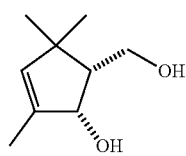

(5C)

wherein hashed unwedged bonds represent a relative configuration, to an esterification reaction, a combination of an esterification reaction with a halogenation reaction, or a combination of an esterification reaction with a sulfonylation reaction to form the 3,5,5-trimethyl-3-cyclopentene compound (1); and
  the aforesaid process for preparing the α-necrodyl compound (3) from the 3,5,5-trimethyl-3-cyclopentene compound (1) thus obtained.

According to another aspect of the present invention, the present invention provides a process for preparing the α-necrodyl compound (3), the process comprising:
  subjecting a 3, 5, 5-trimethyl-2-oxo-3-cyclopentene-1-carboxylate ester compound of the following general formula (6):

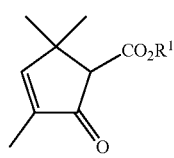

(6)

wherein $R^1$ represents a monovalent hydrocarbon group having 1 to 10 carbon atoms, to a reduction reaction to form (1RS,2SR)-(2-hydroxy-3,5,5-trimethyl-3-cyclopentenyl)methanol (5C), and;
  the aforesaid process for preparing the α-necrodyl compound (3) from the (1RS,2SR)-(2-hydroxy-3,5,5-trimethyl-3-cyclopentenyl)methanol (5C) thus prepared.

According to another aspect of the present invention, the present invention provides a process for preparing the α-necrodyl compound (3), the process comprising:

converting a 3, 5, 5-trimethyl-2-oxo-3-cyclopentene-1-carboxylate ester compound of the following general formula (6):

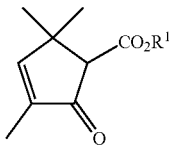

(6)

wherein R¹ represents a monovalent hydrocarbon group having 1 to 10 carbon atoms, into a corresponding carboxylic acid, and subjecting the carboxylic acid thus obtained to a reduction reaction to form (1RS,2SR)-(2-hydroxy-3,5,5-trimethyl-3-cyclopentenyl)methanol (5C), and the aforesaid process for preparing the α-necrodyl compound (3) from the (1RS,2SR)-(2-hydroxy-3,5,5-trimethyl-3-cyclopentenyl)methanol (5C) thus obtained.

According to another aspect of the present invention, the present invention provides (2-hydroxy-3,5,5-trimethyl-3-cyclopentenyl)methanol of the following formula (5):

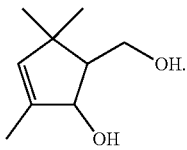

(5)

According to the present invention, it is possible to prepare an α-necrodyl compound and a γ-necrodyl compound in high yields without a special equipment. According to the present invention, it is further possible to provide (1RS,2SR)-(2-hydroxy-3,5,5-trimethyl-3-cyclopentenyl)methanol, which is a useful intermediate for the preparation of an α-necrodyl compound and a γ-necrodyl compound.

DETAILED DESCRIPTION OF THE PREFERRED EMBODIMENTS

Embodiments of the present invention will be described in detail below. It should be noted that the present invention is not limited to or by the embodiments. The intermediates, the reagents, and the target compounds represented by the chemical formulae in the present specification may comprise some stereoisomers such as enantiomers or diastereomers. Unless otherwise stated, the chemical formulae shall be interpreted to represent all of these isomers. The isomer may be a single one alone or in combination thereof.

A. An α-necrodyl compound and a γ-necrodyl compound that are prepared in a process according to the present invention will be described below.

(a) α-Necrodyl Compound

The term "α-necrodyl compound" refers to a group of compounds having a (3,4,5,5-tetramethyl-2-cyclopentenyl) methyl group.

A target compound in the present invention is an α-necrodyl carboxylate compound of the following general formula (3):

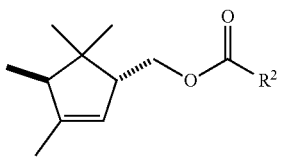

(3)

among the α-necrodyl compounds.

The bold unwedged bond and the hashed unwedged bond in the general formula (3) represent a relative configuration.

R² in the general formula (3) represents a monovalent hydrocarbon group having 1 to 9, preferably 1 to 5, carbon atoms.

Examples of the monovalent hydrocarbon group of R² include linear saturated hydrocarbon groups such as a methyl group, an ethyl group, an n-propyl group, an n-butyl group, an n-pentyl group, an n-hexyl group, an n-heptyl group, an n-octyl group, and an n-nonyl group; branched saturated hydrocarbon groups such as an isopropyl group, a 2-methylbutyl group, and a t-butyl group; cyclic saturated hydrocarbon groups such as a cyclopropyl group, a cyclobutyl group, a cyclopentyl group, a cyclohexyl group, and a cyclopentylmethyl group; linear unsaturated hydrocarbon groups such as a vinyl group, an allyl group, and an ethynyl group; branched unsaturated hydrocarbon groups such as an isopropenyl group and a 2-methyl-2-propenyl group; cyclic unsaturated hydrocarbon groups such as a phenyl group, a tolyl group, a dimethylphenyl group, a benzyl group, and a phenethyl group; and isomers thereof. A part of the hydrogen atoms in the hydrocarbon group may be substituted with a monovalent hydrocarbon group having 1 to 8 carbon atoms.

Specifically, the general formula (3) represents a (1R,4R)-α-necrodyl compound of the following general formula (3-1), a (1S,4S)-α-necrodyl compound of the following general formula (3-2), or both.

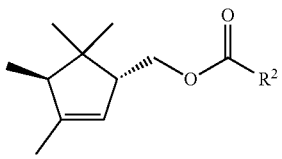

(3-1)

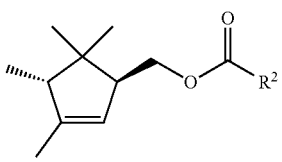

(3-2)

The bold wedged bonds and the hashed wedged bonds in the general formulae (3-1) and (3-2) represent absolute configurations.

Specific examples of the α-necrodyl compound (3) include (1RS,4RS)-(3,4,5,5-tetramethyl-2-cyclopentenyl) methyl isobutyrate of the following formula (3A; or R²=isopropyl group in the general formula (3)) (that is, R² in the general formula (3-1), (3-2) or a combination thereof is an isopropyl group), (1RS,4RS)-(3,4,5,5-tetramethyl-2-cyclopentenyl)methyl acetate (that is, R² in the general formula (3-1), (3-2) or a combination thereof is a methyl group), and (1RS,4RS)-(3,4,5,5-tetramethyl-2-cyclopentenyl)methyl benzoate (that is, $R^2$ in the general formula (3-1), (3-2) or a combination of these is a phenyl group). Among these, (1RS,4RS)-(3,4,5,5-tetramethyl-2-cyclopentenyl) methyl isobutyrate (3A) is preferred in view of the preparation of sex pheromones of grape mealybug and spherical mealybug.

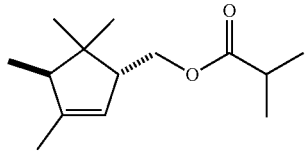

(3A)

The bold unwedged bond and the hashed unwedged bond in the general formula (3A) represent a relative configuration.

(b) γ-Necrodyl Compound

The term "γ-necrodyl compound" refers to a group of compounds having a (2,2,3,4-tetramethyl-3-cyclopentenyl) methyl group.

A target compound in the present invention is a γ-necrodyl carboxylate compound of the following general formula (4):

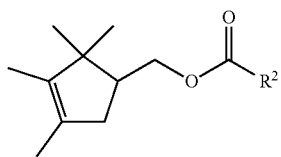

(4)

among the γ-necrodyl compounds.

$R^2$ in the general formula (4) is as defined for the general formula (3).

Specifically, the general formula (4) represents a (1R)-γ-necrodyl compound of the following general formula (4-1), a (1S)-γ-necrodyl compound of the following general formula (4-2), or both.

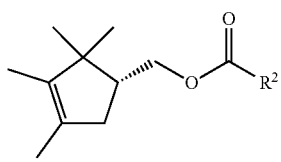

(4-1)

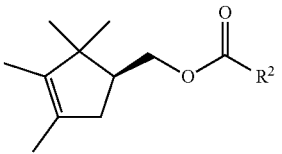

(4-2)

The bold wedged bond in the general formula (4-1) and a hashed wedged bond in the general formula (4-2) represent absolute configurations.

Specific examples of the γ-necrodyl compound (4) include (1RS)-(2,2,3,4-tetramethyl-3-cyclopentenyl)methyl isobutyrate of the following formula (4A) (that is, $R^2$ in the general formula (4-1), (4-2) or a combination thereof is an isopropyl group), (1RS)-(2,2,3,4-tetramethyl-3-cyclopentenyl)methyl acetate (that is, $R^2$ in the general formula (4-1), (4-2) or a combination thereof is a methyl group), and (1RS)-(2,2,3,4-tetramethyl-3-cyclopentenyl)methyl benzoate (that is, $R^2$ in the general formula (4-1), (4-2) or a combination thereof is a phenyl group). Among these, (1RS)-(2,2,3,4-tetramethyl-3-cyclopentenyl)methyl isobutyrate (4A) is preferred in view of the preparation of sex pheromones of grape mealybug and spherical mealybug.

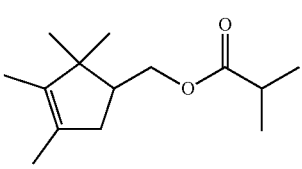

(4A)

B. Next, a process for preparing the α-necrodyl compound (3) and a process for preparing the γ-necrodyl compound (4) according to the present invention will be described below.

The present inventors have contemplated a plan for synthesis of the α-necrodyl compounds (3) and the γ-necrodyl compounds (4), as described below.

Retrosynthetic analysis is represented by the following reaction formula for (1RS)-(2,2,3,4-tetramethyl-3-cyclopentenyl)methyl isobutyrate (4A) as an example of the target compounds, γ-necrodyl compound (4).

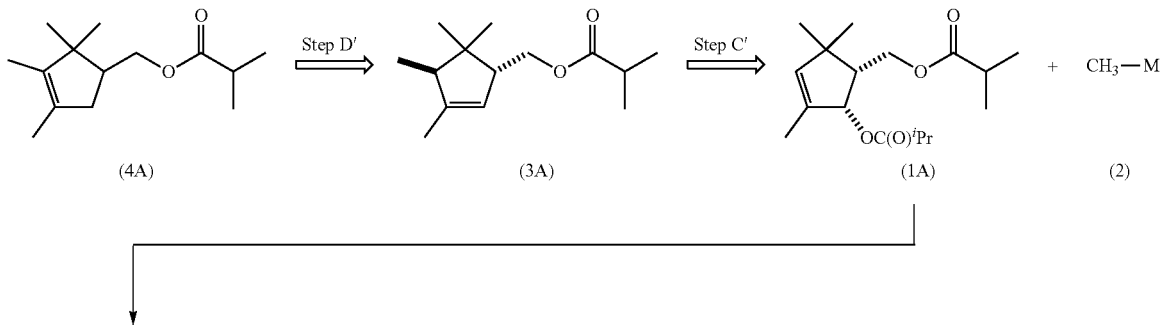

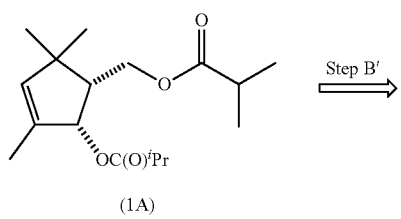
(1A)

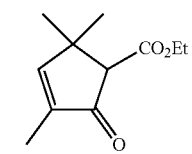
(5C)

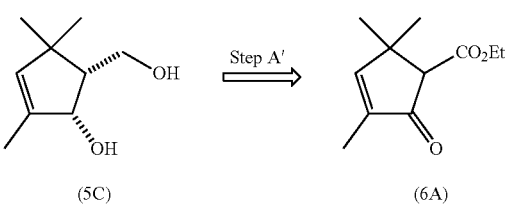
(6A)

In reaction formulae of the retrosynthetic analysis shown above, the open arrows represent transformation in the retrosynthetic analysis. ${}^{i}$Pr represents an isopropyl group, M represents a cationic moiety, and Et represents an ethyl group. The bold unwedged bond in the general formula (3A) and hashed unwedged bonds in the formulae (3A), (1A), and (5C) represent relative configurations.

Step A' A target compound (1RS,2SR)-(2-hydroxy-3,5,5-trimethyl-3-cyclopentenyl)methanol (5C) is thought to be synthesized by stereoselectively subjecting ethyl 2-oxo-3-cyclopentene-1-carboxylate of formula (6A) to a reduction reaction in the reaction formulae.

The reaction formulae obtained from the retrosynthetic analysis shown above has led to reaction formulae according to an embodiment of the present invention as shown below:

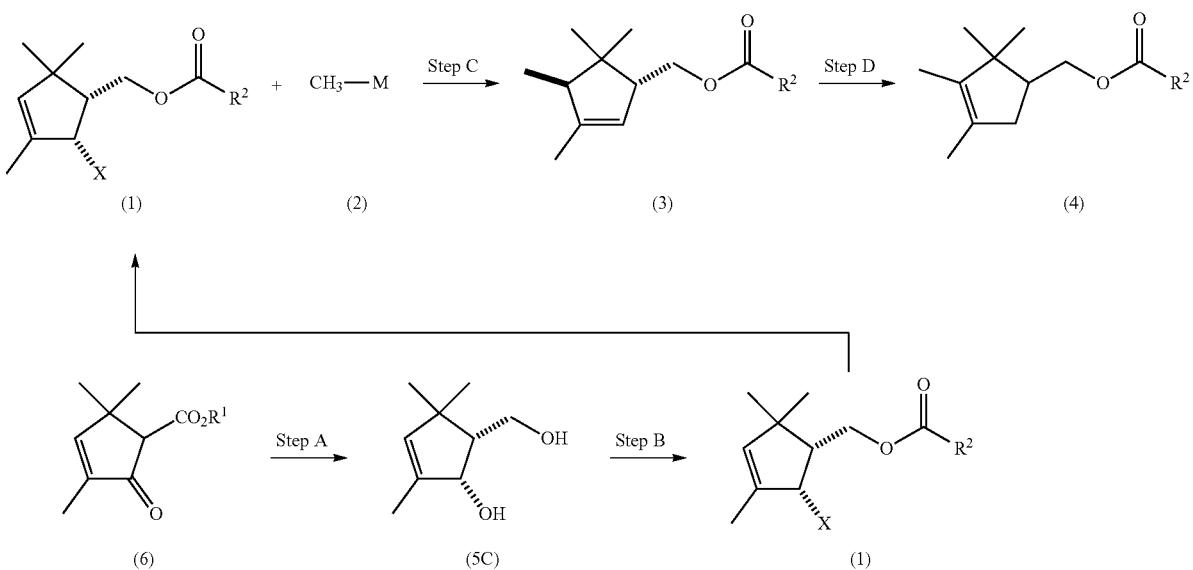

Step D' A target compound (1RS)-(2,2,3,4-tetramethyl-3-cyclopentenyl)methyl isobutyrate (4A) is thought to be synthesized via positional isomerization of the double bond in the (1RS,4RS)-(3,4,5,5-tetramethyl-2-cyclopentenyl) methyl isobutyrate (3A) among α-necrodyl compounds (3). This is because the tetrasubstituted double bond in (1RS)-(2,2,3,4-tetramethyl-3-cyclopentenyl)methyl isobutyrate (4A) is probably more stable than the trisubstituted double bond in (1RS,4RS)-(3,4,5,5-tetramethyl-2-cyclopentenyl) methyl isobutyrate (3A).

Step C' A target compound (1RS,4RS)-(3,4,5,5-tetramethyl-2-cyclopentenyl)methyl isobutyrate (3A) is thought to be synthesized via a regio- and stereoselective nucleophilic substitution reaction between (1RS,2SR)-(3,5,5-trimethyl-2-isobutyryloxy-3-cyclopentenyl)methyl isobutyrate of formula (1A) in the reaction formulae and a methylating agent of formula (2) in the reaction formulae.

Step B' A target compound (1RS,2SR)-(3,5,5-trimethyl-2-isobutyryloxy-3-cyclopentenyl)methyl isobutyrate (1A) is thought to be synthesized by esterifying (1RS,2SR)-(2-hydroxy-3,5,5-trimethyl-3-cyclopentenyl)methanol of formula (5C) in the reaction formulae.

Step A 3,5,5-Trimethyl-2-oxo-3-cyclopentene-1-carboxylate ester compound of the formula (6) in the reaction formulae is stereoselectively reduced to form (1RS,2SR)-(2-hydroxy-3,5,5-trimethyl-3-cyclopentenyl)methanol (5C).

Step B The (1RS,2SR)-(2-hydroxy-3,5,5-trimethyl-3-cyclopentenyl)methanol (5C) formed according to step A or otherwise is subjected to a reachon(s) selected from an esterification reaction, an esterification reaction with a halogenation reaction, and an esterification reaction with a sulfonylation reaction to form a 3,5,5-trimethyl-3-cyclopentene compound of formula (1) in the reaction formulae.

Step C The 3,5,5-trimethyl-3-cyclopentene compound (1) formed according to step B or otherwise is subjected to a nucleophilic substitution reaction with a methylating agent (2) to regio- and stereoselectively introduce a methyl group and form an α-necrodyl compound (3).

Step D The α-necrodyl compound (3) formed according to step C is subjected to a positional isomerization reaction of its double bond to form a γ-necrodyl compound (4).

The steps A to D, which are embodiments of the present invention, will be described in detail below. Step C in which a target compound of the present invention α-necrodyl compound (3) is synthesized, step D in which the γ-necrodyl compound (4), another target compound of the present invention is synthesized, step B in which a starting material of the step C is synthesized, and step A in which a starting material of the step B is synthesized will be described in sequence. In the description of step A, a process for synthesizing (2-hydroxy-3,5,5-trimethyl-3-cyclopentenyl)methanol of formula (5) shown below without stereoselectively subjecting the 3,5,5-trimethyl-2-oxo-3-cyclopentene-1-carboxylate ester compound (6) to a reduction reaction will be also described.

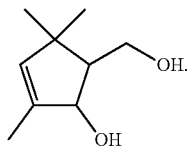

(5)

[1] Step C

Step C in which an α-necrodyl compound (3) is synthesized will be described below. The α-necrodyl compound (3) is synthesized by performing a nucleophilic substitution reaction between the 3,5,5-trimethyl-3-cyclopentene compound (1) and the methylating agent (2), as shown in the following chemical reaction formula:

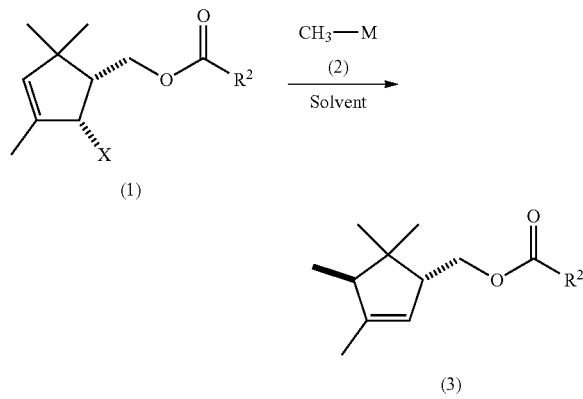

The hashed unwedged bonds in the general formula (1) and (3) and the bold unwedged bond in the general formula (3) represent relative configurations.

In the general formula (1), $R^2$ represents a monovalent hydrocarbon group having 1 to 9, preferably 1 to 5 carbon atoms.

Examples of the monovalent hydrocarbon group include linear saturated hydrocarbon groups such as a methyl group, an ethyl group, an n-propyl group, an n-butyl group, an n-pentyl group, an n-hexyl group, an n-heptyl group, an n-octyl group, and an n-nonyl group; branched saturated hydrocarbon groups such as an isopropyl group, a 2-methylbutyl group, and a t-butyl group; cyclic saturated hydrocarbon groups such as a cyclopropyl group, a cyclobutyl group, a cyclopentyl group, a cyclohexyl group, and a cyclopentylmethyl group; linear unsaturated hydrocarbon groups such as a vinyl group, an allyl group, and an ethynyl group; branched unsaturated hydrocarbon groups such as an isopropenyl group and a 2-methyl-2-propenyl group; cyclic unsaturated hydrocarbon groups such as a phenyl group, a tolyl group, a dimethylphenyl group, a benzyl group, and a phenethyl group; and isomers thereof. A part of the hydrogen atoms in the hydrocarbon groups may be substituted with a monovalent hydrocarbon group having 1 to 8 carbon atoms.

For the preparation of sex pheromones of grape mealybug and spherical mealybug, $R^2$ is preferably an isopropyl group, because the target compound whose $R^2$ is an isopropyl group can be directly formed without replacing the acyl group.

The leaving group X in general formula (1) represents an acyloxy group having 1 to 10 carbon atoms including a carbon atom of a carbonyl group; an alkanesulfonyloxy group having 1 to 10 carbon atoms; an arenesulfonyloxy group having 6 to 20 carbon atoms; or a halogen atom.

Examples of the acyloxy group having 1 to 10 carbon atoms including a carbon atom of a carbonyl group include linear acyloxy groups such as a formyloxy group, an acetoxy group, a propionyloxy group, a butyryloxy group, a valeryloxy group, a hexanoyloxy group, a heptanoyloxy group, an octanoyloxy group, a nonanoyloxy group, a decanoyloxy group, and a crotonyloxy group; branched acyloxy groups such as an isobutyryloxy group, a pivaloyloxy group, a 2-methylbutanoyloxy group, a 3-methyl-2-butenoyloxy group, and a 3-methyl-3-butenoyloxy group; cyclic acyloxy groups such as a cyclohexylcarbonyloxy group and a benzoyloxy group; halogenated acyloxy groups such as a trichloroacetoxy group and a trifluoroacetoxy group; and isomers thereof. A part of the hydrogen atoms in the acyloxy groups may be substituted with a monovalent hydrocarbon group having 1 to 8 carbon atoms or with a halogen atom. Examples of the halogen atom include a chlorine atom, a bromine atom, and an iodine atom.

Among the acyloxy groups, a formyloxy group, an acetoxy group, a propionyloxy group, a pivaloyloxy group, an isobutyryloxy group, and a benzoyloxy group are preferred in view of the availability.

Examples of the alkanesulfonyloxy groups having 1 to 10 carbon atoms include a methanesulfonyloxy group, an ethanesulfonyloxy group, a 1-butanesulfonyloxy group, a 1-pentanesulfonyloxy group, a 1-hexanesulfonyloxy group, a 1-heptanesulfonyloxy group, a 1-octanesulfonyloxy group, a 1-nonanesulfonyloxy group, a 1-decanesulfonyloxy group, an allylsulfonyloxy group, a 10-camphorsulfonyloxy group, a trifluoromethanesulfonyloxy group, an α-benzylsulfonyloxy group, and isomers thereof. A part of the hydrogen atoms in the alkanesulfonyloxy groups may be substituted with a methyl group, an ethyl group, or a halogen atom. Examples of the halogen atom include a chlorine atom, a bromine atom, and an iodine atom. Among the alkanesulfonyloxy groups, a methanesulfonyloxy group and an ethanesulfonyloxy group are preferred in view of the availability.

Examples of the arenesulfonyloxy groups having 6 to 20 carbon atoms include a benzenesulfonyloxy group, a 4-chlorobenzenesulfonyloxy group, a 4-methoxybenzenesulfonyloxy group, a 2-nitrobenzenesulfonyloxy group, a 2,4,6-trimethylbenzenesulfonyloxy group, a p-toluenesulfonyloxy group, a 1-naphthalenesulfonyloxy group, a 2-naphthalenesulfonyloxy group, and isomers thereof. A part of the hydrogen atoms in the arenesulfonyloxy groups may be substituted with a methyl group, an ethyl group, or a halogen atom. Examples of the halogen atom include a fluorine atom, a chlorine atom, a bromine atom, and an iodine atom.

Among the arenesulfonyloxy groups, a benzenesulfonyloxy group and a p-toluenesulfonyloxy group are preferred in view of the availability.

Examples of the halogen atom include a fluorine atom, chlorine atom, a bromine atom, and an iodine atom. Among the halogen atoms, a chlorine atom and a bromine atom are preferred in view of the availability.

The leaving group X is preferably an acyloxy group or a halogen atom. For the preparation of sex pheromones of grape mealybug and spherical mealybug, the leaving group X is more preferably an acyloxy group, and is even more preferably an isobutyryloxy group, because $R^2$ in the target compound is an isopropyl group, and the primary alcohol and secondary alcohol of (1RS,2SR)-(2-hydroxy-3,5,5-trimethyl-3-cyclopentenyl)methanol (5C) can be simultaneously esterified.

Specifically, the general formula (1) represents a (1R,2S)-3,5,5-trimethyl-3-cyclopentene compound of the following general formula (1-1), a (1S,2R)-3,5,5-trimethyl-3-cyclopentene compound of the following general formula (1-2), or both.

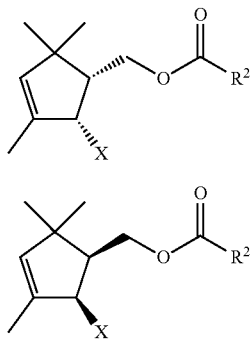

(1-1)

(1-2)

The hashed wedged bonds in the general formula (1-1) and the bold wedged bonds in the general formula (1-2) represent absolute configurations.

Specific examples of the 3,5,5-trimethyl-3-cyclopentene compound (1) include (1RS,2SR)-(3,5,5-trimethyl-2-acyloxy-3-cyclopentenyl)methyl carboxylate, such as (1RS,2SR)-(3,5,5-trimethyl-2-isobutyryloxy-3-cyclopentenyl)methyl isobutyrate of the following formula (1A; or $R_2$=isopropyl group and X=isobutyryloxy group in the general formula (1)); (1RS,2SR)-(3,5,5-trimethyl-2-alkylsulfonyloxy-3-cyclopentenyl)methyl carboxylate, such as (1RS,2SR)-(3,5,5-trimethyl-2-methanesulfonyloxy-3-cyclopentenyl)methyl acetate; and (1RS,2SR)-(3,5,5-trimethyl-2-halo-3-cyclopentenyl)methyl carboxylate, such as (1RS,2SR)-(3,5,5-trimethyl-2-bromo-3-cyclopentenyl) methyl isobutyrate. (1RS,2SR)-(3,5,5-trimethyl-2-isobutyryloxy-3-cyclopentenyl)methyl isobutyrate (1A) is preferred in view of the preparation of sex pheromones of grape mealybug and spherical mealybug.

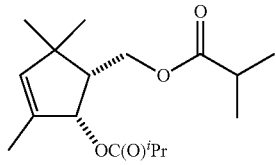

(1A)

The hashed unwedged bonds in the general formula (1A) represent a relative configuration.

Specifically, formula (1A) represents (1R,2S)-(3,5,5-trimethyl-2-isobutyryloxy-3-cyclopentenyl)methyl isobutyrate of the following formula (1A-1), (1S,2R)-(3,5,5-trimethyl-2-isobutyryloxy-3-cyclopentenyl)methyl isobutyrate of the following formula (1A-2), or both.

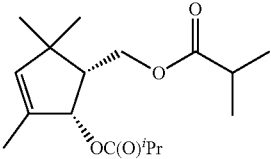

(1A-1)

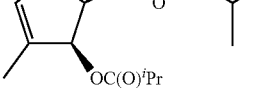

(1A-2)

The hashed wedged bonds in the general formula (1A-1) and the bold wedged bonds in the general formula (1A-2) represent absolute configurations.

3,5,5-Trimethyl-3-cyclopentene compound (1) and (1RS,2SR)-(3,5,5-trimethyl-2-isobutyryloxy-3-cyclopentenyl) methyl isobutyrate (1A) may be synthesized according to step B which will be described in detail below, or in other methods.

A methylating agent (2) is used in the nucleophilic substitution reaction. An organometallic reagent comprising a metal element of Group I or Group II or a transition metal element is typically used in the nucleophilic substitution reaction.

M in the methylating agent (2) represents Li, $MgZ^1$, $ZnZ^1$, Cu, $CuZ^1$, or $CuLiZ^1$, and $Z^1$ represents a halogen atom or a methyl group. Examples of the halogen atom $Z^1$ include a chlorine atom, a bromine atom, and an iodine atom.

The methylating agent (2) is preferably an organolithium reagent, such as methyl lithium; and an organomagnesium reagent, such as a Grignard reagent and a methylmagnesium halide, particularly a Grignard reagent, in view of the selectivity and/or ease of the preparation.

The methylating agent (2) may be prepared in a metal exchange reaction between an organolithium or organomagnesium reagent and a stoichiometric amount (1 mol or more) of a transition metal compound, or via an in-situ reaction between an organolithium or a Grignard reagent and a catalytic amount of a transition metal compound.

Examples of the transition metal compound include transition metal compounds comprising copper, iron, nickel, palladium, zinc, or silver; cuprous halides, such as copper (I) chloride, copper (I) bromide, and copper (I) iodide; cupric halides, such as copper (II) chloride, copper (II) bromide, and copper (II) iodide; copper cyanides, such as copper (I) cyanide and copper (II) cyanide; copper oxides, such as copper (I) oxide and copper (II) oxide; and copper compounds, such as dilithium tetrachlorocuprate ($Li_2CuCl_4$). Copper (including cupric and cuprous) halides are preferred in view of the reactivity.

An amount of the transition metal compound used is preferably from 0.01 to 10 mol, and more preferably 0.1 to 5 mol, per mol of the 3,5,5-trimethyl-3-cyclopentene compound (1), in view of the reactivity and selectivity.

When a transition metal compound is used in the nucleophilic substitution reaction, a co-catalyst may be used preferably in an amount of 0.01 to 1,000 parts by weight per 100 parts by weight of the transition metal compound to improve the solubility of the transition metal compound in a solvent.

Specific examples of the co-catalyst include phosphorus compounds, such as trialkyl phosphites such as triethyl phosphite, and triarylphosphines such as triphenylphosphine.

In the nucleophilic substitution reaction, a lithium salt such as lithium chloride, lithium bromide, or lithium iodide may be present as a catalyst for the reaction in an amount of 0.001 to 1,000 mol per mol of the 3,5,5-trimethyl-3-cyclopentene compound (1). A combination of a copper halide and the lithium salt is preferred in view of the reactivity and selectivity.

An amount of the methylating agent (2) used may be optionally determined while considering the reagents, the reaction conditions, the reaction yield, the cost efficiency including prices of intermediates, and/or ease of isolation and purification of the target compound from reaction mixture, and is preferably from 0.2 to 100 mol, more preferably 0.5 to 20 mol, and even more preferably 0.8 to 5 mol, per mol of the 3,5,5-trimethyl-3-cyclopentene compound (1).

Examples of the solvent used in the nucleophilic substitution reaction include ether solvents such as tetrahydrofuran, 4-methyltetrahydropyran, diethyl ether, t-butyl methyl ether, and 1,4-dioxane; hydrocarbon solvents such as toluene, xylene, and hexane; and polar solvents such as N,N-dimethylformamide, N,N-dimethylacetamide, acetonitrile, dichloromethane, and chloroform. Tetrahydrofuran is preferred in view of the reactivity and solubility.

The solvent may be used either alone or in combination thereof, if necessary. The solvent may be commercially available one.

An amount of the solvent used varies, depending on a production scale, and is preferably from 200 to 4,000 g per mol of the 3,5,5-trimethyl-3-cyclopentene compound (1) in view of the reaction rate.

A reaction temperature in the preparation of the α-necrodyl compound (3) is preferably from −78 to 150° C., more preferably −78 to 80° C., in view of the reactivity and suppression of by-product formation.

A reaction time in the preparation of the α-necrodyl compound (3) varies, depending on a solvent and/or a reaction scale, and is preferably from 0.1 to 120 hours.

(1RS,4RS)-(3,4,5,5-tetramethyl-2-cyclopentenyl)methyl isobutyrate (3A) among the α-necrodyl compounds (3) may be synthesized by a nucleophilic substitution reaction between (1RS,2SR)-(3,5,5-trimethyl-2-isobutyryloxy-3-cyclopentenyl)methyl isobutyrate (1A) and the methylating agent (2), as shown in the following chemical reaction formula (also see Example 1 below).

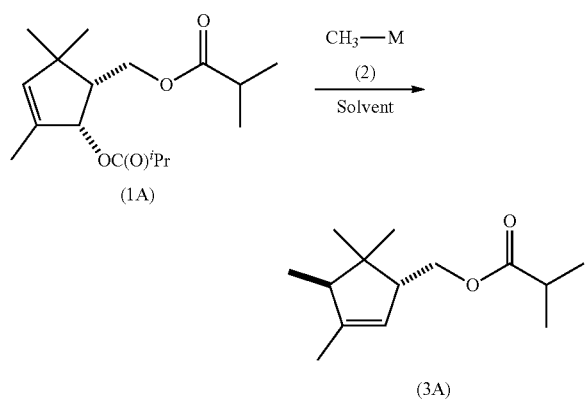

[2] Step D

Step D to synthesize the γ-necrodyl compound (4) will be described below. The γ-necrodyl compound (4) is synthesized by subjecting the α-necrodyl compound (3) synthesized in step C to a positional isomerization reaction of its double bond, as shown in the following chemical reaction formula.

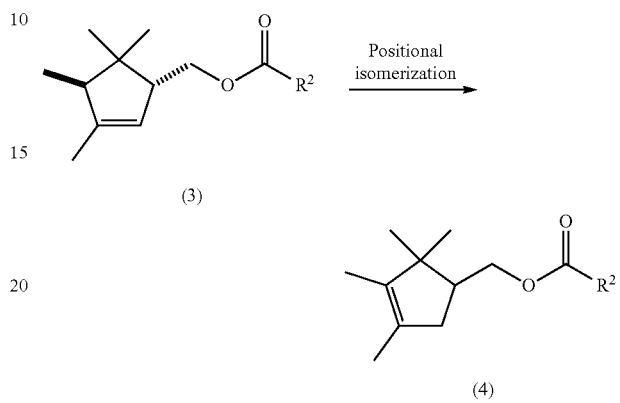

The isomerization reaction of the double bond occurs in the presence of a reagent in a solvent, if needed, with cooling or heating.

Examples of the reagent for the isomerization reaction of the double bond include alkaline metal-ethylenediamine in ethylenediamine such as lithium-ethylenediamine in ethylenediamine; Lewis acids such as boron trifluoride-ethyl ether complex; inorganic acids such as hydrochloric acid, hydrobromic acid, nitric acid, and sulfuric acid; and p-toluenesulfonic acid, trifluoroacetic acid, acetic acid, formic acid, and oxalic acid. p-Toluenesulfonic acid is preferred in view of the reactivity and ease of handling.

An amount of the reagent used in the isomerization reaction of the double bond is preferably from 0.0001 to 100 mol, more preferably 0.001 to 10 mol, even more preferably 0.01 to 1 mol, per mol of the α-necrodyl compound (3) in view of the reactivity.

Examples of the solvent used in the isomerization of the double bond include ether solvents such as tetrahydrofuran, 4-methyltetrahydropyran, diethyl ether, t-butyl methyl ether, and 1,4-dioxane; hydrocarbon solvents such as toluene, xylene, and hexane; and polar solvents such as N,N-dimethylformamide, N,N-dimethylacetamide, acetonitrile, dichloromethane, and chloroform. Hydrocarbon solvents such as toluene are preferred in view of the reaction rate.

The solvent may be used either alone or in combination thereof, if necessary. The solvent may be commercially available one.

An amount of the solvent used varies, depending on a production scale, and is preferably from 200 to 8,000 g per mol of the α-necrodyl compound (3) in view of the reaction rate.

A reaction temperature in the isomerization of the double bond is preferably from −78° C. to a boiling point temperature of the solvent, and more preferably 0 to 150° C., in view of the reaction rate and suppression of by-product formation.

A reaction time of the isomerization of the double bond varies, depending on a solvent and/or a reaction scale to be used, and is preferably from 0.1 to 120 hours.

(1RS)-(2,2,3,4-tetramethyl-3-cyclopentenyl)methyl isobutyrate (4A) among the γ-necrodyl compounds (4) may be synthesized by a positional isomerization reaction of the double bond of the (1RS,4RS)-(3,4,5,5-tetramethyl-2-cyclopentenyl)methyl isobutyrate (3A), as shown in the following chemical reaction formula (also see Example 2 below).

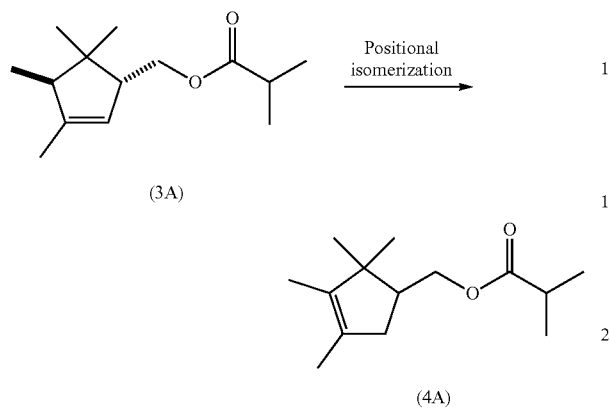

(3A)

(4A)

Specifically, formula (3A) represents (1R,4R)-(3,4,5,5-tetramethyl-2-cyclopentenyl)methyl isobutyrate of the following formula (3A-1), (1 S,4S)-(3,4,5,5-tetramethyl-2-cyclopentenyl)methyl isobutyrate of the following formula (3A-2), or both.

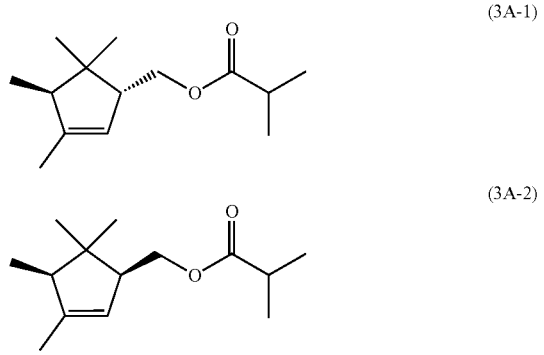

(3A-1)

(3A-2)

The bold wedged bond and the hashed wedged bond in the general formulae (3A-1) and (3A-2) represent absolute configurations.

[3] Step B

Step B to synthesize 3,5,5-trimethyl-3-cyclopentene compound (1) will be described below. 3,5,5-Trimethyl-3-cyclopentene compound (1) is synthesized by subjecting (1RS, 2SR)-(2-hydroxy-3,5,5-trimethyl-3-cyclopentenyl) methanol (5C) to (i) an esterification reaction, (ii) a combination of an esterification reaction and a halogenation reaction, or (iii) a combination of an esterification reaction and a sulfonylation reaction, as shown in the following chemical reaction formula. The reaction(s) is chosen in view of the reactivity, reaction selectivity, availability, ease of synthesis, storage stability, toxicity, and/or prices.

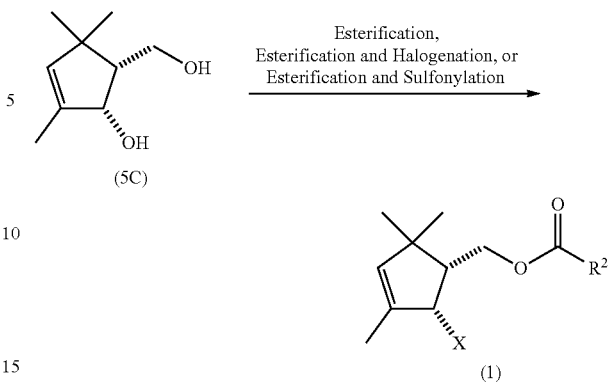

(5C)

(1)

3,5,5-Trimethyl-3-cyclopentene compound (1) is as described above.

The esterification reactions in (i), (ii), and (iii) described above may be done in any known process for preparing an ester, such as a reaction with an acylating agent, a reaction with a carboxylic acid, or a transesterification reaction.

For the reaction with an acylating agent, (1RS,2SR)-(2-hydroxy-3,5,5-trimethyl-3-cyclopentenyl)methanol (5C) is sequentially or simultaneously contacted with an acylating agent in a solvent in the presence of a base.

Examples of the acylating agent include acyl halides such as acetyl chloride, isobutyryl chloride, and benzoyl chloride; carboxylic anhydrides such as acetic anhydride and isobutyric anhydride; carboxylic mixed anhydrides such as carboxylic/trifluoroacetic acid mixed anhydride, carboxylic/methanesulfonic acid mixed anhydride, carboxylic/trifluoromethanesulfonic acid mixed anhydride, carboxylic/benzenesulfonic acid mixed anhydride, and carboxylic/p-toluenesulfonic acid mixed anhydride; and p-nitrophenyl carboxylate.

An amount of the acylating agent used is preferably from 1 to 500 mol, more preferably 1 to 50 mol, even more preferably 1 to 5 mol, per mol of (1RS,2SR)-(2-hydroxy-3, 5,5-trimethyl-3-cyclopentenyl)methanol (5C).

Examples of the base used in the reaction with the acylating agent include diisopropylethylamine, N,N-dimethylaniline, N,N-diethylaniline, pyridine, 2-ethyl pyridine, and 4-dimethylaminopyridine.

An amount of the base used is preferably from 1 to 500 mol, per mol of (1RS,2SR)-(2-hydroxy-3,5,5-trimethyl-3-cyclopentenyl)methanol (5C).

The solvent used in the reaction with the acylating agent may be the base itself described above, or may be an ether solvent such as tetrahydrofuran, 4-methyltetrahydropyran, diethyl ether, t-butyl methyl ether, and 1,4-dioxane; a hydrocarbon solvent such as toluene, xylene, and hexane; and a polar solvent such as N,N-dimethylformamide, N,N-dimethylacetamide, acetonitrile, dichloromethane, and chloroform.

The solvent may be used either alone or in combination thereof, if necessary. The solvent may be commercially available one.

An amount of the solvent used is preferably from 0 to 100,000 g, and more preferably 0 to 10,000 g, per mol of (1RS,2SR)-(2-hydroxy-3,5,5-trimethyl-3-cyclopentenyl) methanol (5C). When the base is used as a solvent, any additional solvent except the base may not be required.

When a carboxylic anhydride, a carboxylic acid mixed anhydride or p-nitrophenyl carboxylate is specifically used as the acylating agent in the reaction, an acid catalyst may be used instead of the base.

Examples of the acid catalyst include inorganic acids such as hydrochloric acid, hydrobromic acid, sulfuric acid, and nitric acid; organic acids such as oxalic acid, trifluoroacetic acid, methanesulfonic acid, benzenesulfonic acid, and p-toluenesulfonic acid; and Lewis acids such as aluminum trichloride, aluminum ethoxide, aluminum isopropoxide, aluminum oxide, boron trifluoride, boron trichloride, boron tribromide, magnesium chloride, magnesium bromide, magnesium iodide, zinc chloride, zinc bromide, zinc iodide, tin tetrachloride, tin tetrabromide, dibutyltin dichloride, dibutyltin dimethoxide, dibutyltin oxide, titanium tetrachloride, titanium tetrabromide, titanium (IV) methoxide, titanium (IV) ethoxide, titanium (IV) isopropoxide, and titanium (IV) oxide.

The acylating agent may be used either alone or in combination thereof, if necessary. The acylating agent may be commercially available one.

An amount of the acid catalyst used in the reaction with the specific acylating agent such as a carboxylic anhydride, a carboxylic acid mixed anhydride, or p-nitrophenyl carboxylate is preferably from 0.0001 to 100 mol, per mol of (1RS,2SR)-(2-hydroxy-3,5,5-trimethyl-3-cyclopentenyl) methanol (5C).

A reaction temperature in the reaction with the acylating agent is preferably from −50 to 150° C., more preferably −20 to 50° C., in view of the reaction rate and suppression of by-product formation.

A reaction time of the reaction with the acylating agent varies, depending on a solvent and/or a reaction scale to be used, and is preferably from 0.1 to 120 hours.

The reaction with a carboxylic acid is a dehydration reaction between (1RS,2SR)-(2-hydroxy-3,5,5-trimethyl-3-cyclopentenyl)methanol (5C) and a carboxylic acid, and is carried out typically in the presence of an acid catalyst.

Specific examples of the carboxylic acid used in the reaction between (1RS,2SR)-(2-hydroxy-3,5,5-trimethyl-3-cyclopentenyl)methanol (5C) and a carboxylic acid include linear saturated carboxylic acids such as formic acid, acetic acid, propionic acid, butyric acid, valeric acid, and caproic acid; branched saturated carboxylic acids such as isobutyric acid, isovaleric acid, 4-methylpentanoic acid, 2-methylbutanoic acid, and pivalic acid; linear unsaturated carboxylic acids such as acrylic acid, crotonic acid, and 3-butenoic acid; branched unsaturated carboxylic acids such as methacrylic acid, senecioic acid, tiglic acid, angelic acid, 3-methyl-4-pentenoic acid, and 4-methyl-4-pentenoic acid; and aromatic carboxylic acids such as benzoic acid.

An amount of the carboxylic acid used is preferably from 1 to 500 mol, more preferably 1 to 50 mol, even more preferably 1 to 5 mol, per mol of (1RS,2SR)-(2-hydroxy-3,5,5-trimethyl-3-cyclopentenyl)methanol (5C).

An acid catalyst may be used in the reaction between (1RS,2SR)-(2-hydroxy-3,5,5-trimethyl-3-cyclopentenyl) methanol (5C) and the carboxylic acid. The acid catalyst may be those used in the reaction with the acylating agent.

An amount of the acid catalyst used is preferably 0.0001 to 100 mol, more preferably 0.001 to 1 mol, even more preferably 0.01 to 0.05 mol, per mol of (1RS,2SR)-(2-hydroxy-3,5,5-trimethyl-3-cyclopentenyl)methanol (5C).

A solvent and its amount used in the reaction between (1RS,2SR)-(2-hydroxy-3,5,5-trimethyl-3-cyclopentenyl) methanol (5C) and the carboxylic acid may be those in the aforesaid reaction with the acylating agent.

A reaction temperature in the reaction of (1RS,2SR)-(2-hydroxy-3,5,5-trimethyl-3-cyclopentenyl)methanol (5C) with the carboxylic acid is preferably from −50 to 150° C., more preferably 0 to 150° C., in view of the reaction rate and suppression of by-product formation.

The reaction may be done in a solvent such as a hydrocarbon solvent, such as hexane, heptane, benzene, toluene, xylene, or cumene, while removing the resulting water out of the system by azeotropic distillation. Alternatively, water may be distilled off with refluxing at the boiling point of the solvent in normal pressure, or distilled off at a lower temperature than the boiling point of water under reduced pressure.

A reaction time in the reaction between (1RS,2SR)-(2-hydroxy-3,5,5-trimethyl-3-cyclopentenyl)methanol (5C) and the carboxylic acid varies, depending on a solvent and/or a reaction scale to be used, and is preferably from 0.1 to 120 hours.

The transesterification reaction is carried out by reacting (1RS,2SR)-(2-hydroxy-3,5,5-trimethyl-3-cyclopentenyl) methanol (5C) with an alkyl carboxylate in the presence of an acid catalyst and removing a resulting alcohol.

The alkyl carboxylate is preferably a primary alkyl ester of a carboxylic acid. Methyl carboxylates, ethyl carboxylates, and n-propyl carboxylates are preferred in view of the price and/or ease of reaction.

Examples of the carboxylic acid include those used in the aforesaid reaction with the carboxylic acid.

An amount of the alkyl carboxylate used is preferably 1 to 500 mol, more preferably 1 to 50 mol, even more preferably 1 to 5 mol, per mol of (1RS,2SR)-(2-hydroxy-3,5,5-trimethyl-3-cyclopentenyl)methanol (5C).

Examples of the acid catalyst used in the transesterification reaction include inorganic acids such as hydrochloric acid, hydrobromic acid, sulfuric acid, and nitric acid; organic acids such as oxalic acid, trifluoroacetic acid, methanesulfonic acid, benzenesulfonic acid, and p-toluenesulfonic acid; and Lewis acids such as aluminum trichloride, aluminum ethoxide, aluminum isopropoxide, aluminum oxide, boron trifluoride, boron trichloride, boron tribromide, magnesium chloride, magnesium bromide, magnesium iodide, zinc chloride, zinc bromide, zinc iodide, tin tetrachloride, tin tetrabromide, dibutyltin dichloride, dibutyltin dimethoxide, dibutyltin oxide, titanium tetrachloride, titanium tetrabromide, titanium (IV) methoxide, titanium (IV) ethoxide, titanium (IV) isopropoxide, and titanium (IV) oxide.

The acid catalyst may be used either alone or in combination thereof, if necessary. The acid catalyst may be commercially available one.

An amount of the acid catalyst used is preferably 0.0001 to 100 mol, more preferably 0.001 to 1 mol, even more preferably 0.01 to 0.05 mol, per mol of (1RS,2SR)-(2-hydroxy-3,5,5-trimethyl-3-cyclopentenyl)methanol (5C).

The transesterification reaction may be carried out with the reactant, alkyl carboxylate, being a solvent without any additional solvent, or with an auxiliary solvent. The former embodiment without any additional solvent is preferred, because this does not require extra operations such as concentration or solvent recovery.

Examples of the solvent used in the transesterification reaction include ether solvents such as tetrahydrofuran, 4-methyltetrahydropyran, diethyl ether, t-butyl methyl ether, and 1,4-dioxane; and hydrocarbon solvents such as toluene, xylene, and hexane.

The solvent may be used either alone or in combination thereof, if necessary. The solvent may be commercially available one.

An amount of the solvent used is preferably 10 to 10,000 g per mol of (1RS,2SR)-(2-hydroxy-3,5,5-trimethyl-3-cyclopentenyl)methanol (5C).

The transesterification reaction may be carried out preferably at a temperature near a boiling point of a lower alcohol that is formed in the transesterification, such as C1-C3 alcohol such as methanol, ethanol, and 1-propanol, while distilling the alcohol off, in view of the reaction rate. The alcohol may be distilled off at a lower temperature than its boiling point under reduced pressure. A reaction time of the transesterification reaction varies, depending on a solvent and/or a reaction scale to be used, and is preferably from 0.1 to 120 hours.

Next, the halogenation reaction to be combined with the esterification reaction in option (ii) will be explained. Any known method for halogenation may be applicable. Examples of the known halogenation reaction methods include a reaction with a halogenating agent or with sulfonic halide.

Examples of the halogenating agent include thionyl halides such as thionyl chloride and thionyl bromide; phosphorus halides such as phosphorous trichloride, phosphorous pentachloride, and phosphorous pentabromide; phosphorus oxyhalides such as phosphorus oxychloride and phosphorus oxybromide; and halogenated aromatic phosphorous compounds such as dichlorotriphenylphosphorane and dibromotriphenylphosphorane.

Examples of the sulfonic halide include methanesulfonyl chloride, ethanesulfonyl chloride, and trifluoromethanesulfonyl chloride. When a sulfonic halide is used, a secondary hydroxy group is sulfonated, and then the resulting sulfonyloxy group can be substituted with a halogen atom by heating, if necessary.

The halogenation reaction is preferably performed in a basic or weakly acidic condition. A preferred example of the halogenation reaction is carried out using a sulfonic halide in the presence of a base. The basic or weakly acidic condition can be selected, for example, by adjusting the amounts of the sulfonic halide and a base.

Examples of the base used in the halogenation reaction include amines such as diethylamine, triethylamine, diisopropylethylamine, tri-n-propylamine, tri-n-butylamine, 1,8-diazabicyclo[5.4.0]-7-undecene, 1,5-diazabicyclo[4.3.0]-5-nonene, N-methylmorpholine, and N,N-dimethylaniline; pyridines such as pyridine, methyl ethyl pyridine, lutidine, and N,N-dimethyl-4-aminopyridine; organic bases such as imidazoles and pyrazoles; inorganic bases, for instance, alkaline metal or alkaline-earth metal hydroxides such as lithium hydroxide, sodium hydroxide, potassium hydroxide, magnesium hydroxide, calcium hydroxide, and barium hydroxide; alkaline metal or alkaline-earth metal carbonates such as sodium carbonate, potassium carbonate, cesium carbonate, magnesium carbonate, calcium carbonate, and barium carbonate; metal alkoxides such as sodium ethoxide; alkaline metal amides such as sodium amide and lithium amide; and alkaline metal hydrides such as sodium hydride and lithium hydride. Specific preferred examples include pyridine and triethylamine.

Examples of the solvent used in the halogenation reaction include ether solvents such as tetrahydrofuran, 4-methyltetrahydropyran, diethyl ether, t-butyl methyl ether, and 1,4-dioxane; hydrocarbon solvents such as toluene, xylene, and hexane; and polar solvents such as N,N-dimethylformamide, N,N-dimethylacetamide, acetonitrile, dichloromethane, and chloroform. Hydrocarbon solvents such as toluene are preferred in view of the reaction rate.

The solvent may be used either alone or in combination thereof, if necessary. The solvent may be commercially available one.

An amount of the solvent used is preferably 10 to 10,000 g per mol of (1RS,2SR)-(2-hydroxy-3,5,5-trimethyl-3-cyclopentenyl)methyl carboxylate compound.

A reaction temperature in the halogenation reaction is preferably from −78 to 150° C., more preferably −10 to 100° C., in view of the reaction rate.

A reaction time of the halogenation reaction varies, depending on a solvent and/or a reaction scale to be used, and is preferably from 0.1 to 120 hours.

Finally, the sulfonylation reaction to be combined with esterification reaction in option (iii) will be explained. Any method for the sulfonylation reaction may be applied. Examples of the known sulfonylation reaction include a reaction with an alkanesulfonylation agent or with an arenesulfonylation agent.

Examples of the alkanesulfonylation agent include alkanesulfonic anhydrides that may be substituted, such as methanesulfonic anhydride, ethanesulfonic anhydride, and trifluoromethanesulfonic anhydride; and alkanesulfonyl halides that may be substituted, such as methanesulfonyl chloride, ethanesulfonyl chloride, and trifluoromethanesulfonyl chloride.

Examples of the arenesulfonylation agent include arenesulfonic anhydrides such as benzenesulfonic anhydride and p-toluenesulfonic anhydride; and arenesulfonyl halides such as benzenesulfonyl chloride and p-toluenesulfonyl chloride.

The sulfonylation reaction is preferably performed under a basic or mild acidic condition, and preferred examples of the sulfonylation reaction include a reaction with a sulfonic halide and base. The basic or mild acidic condition can be selected, for example, by adjusting the amounts of the sulfonic halide and base.

Examples of the base used in the sulfonylation reaction include amines such as diethylamine, triethylamine, diisopropylethylamine, tri-n-propylamine, tri-n-butylamine, 1,8-diazabicyclo[5.4.0]-7-undecene, 1,5-diazabicyclo[4.3.0]-5-nonene, N-methylmorpholine, and N,N-dimethylaniline; pyridines such as pyridine, methyl ethyl pyridine, lutidine, and N,N-dimethyl-4-aminopyridine; organic bases such as imidazoles and pyrazoles; inorganic bases, for instance, alkaline metal or alkaline-earth metal hydroxides such as lithium hydroxide, sodium hydroxide, potassium hydroxide, magnesium hydroxide, calcium hydroxide, and barium hydroxide; alkaline metal or alkaline-earth metal carbonates such as sodium carbonate, potassium carbonate, cesium carbonate, magnesium carbonate, calcium carbonate, and barium carbonate; metal alkoxides such as sodium ethoxide; alkaline metal amides such as sodium amide and lithium amide; and alkaline metal hydrides such as sodium hydride and lithium hydride. Specific preferred examples include pyridine and triethylamine.

Examples of the solvent used in the sulfonylation reaction include ether solvents such as tetrahydrofuran, 4-methyltetrahydropyran, diethyl ether, t-butyl methyl ether, and 1,4-dioxane; hydrocarbon solvents such as toluene, xylene, and hexane; and polar solvents such as N,N-dimethylformamide, N,N-dimethylacetamide, acetonitrile, dichloromethane, and chloroform. Hydrocarbon solvents such as toluene are preferred in view of the reaction rate.

The solvent may be used either alone or in combination thereof, if necessary. The solvent may be commercially available one.

An amount of the solvent used is preferably 10 to 10,000 g per mol of (1RS,2SR)-(2-hydroxy-3,5,5-trimethyl-3-cyclopentenyl)methyl carboxylate compound.

A reaction temperature in the sulfonylation reaction is preferably from −78 to 150° C., more preferably −10 to 100° C., in view of the reaction rate.

A reaction time of the sulfonylation reaction varies, depending on a solvent and/or a reaction scale to be used, and is preferably from 0.1 to 120 hours.

Selection among options (A) the esterification reaction; (B) the combination of the esterification reaction with the halogenation reaction; and (C) the combination of the esterification reaction with the sulfonylation reaction is made, based on, for example, the leaving group X, as described below.

When the leaving group X is an acyloxy group, the esterification reaction is selected for conversion of the secondary hydroxy group of a compound having a 3,5,5-trimethyl-3-cyclopentene group.

When the leaving group X is a halogen atom, the primary hydroxy group of (1RS,2SR)-(2-hydroxy-3,5,5-trimethyl-3-cyclopentenyl)methanol (5C) is esterified, and then the secondary hydroxy group is converted with the halogenating agent.

When the leaving group X is an alkanesulfonyloxy group, the primary hydroxy group of (1RS,2SR)-(2-hydroxy-3,5,5-trimethyl-3-cyclopentenyl)methanol (5C) is esterified, and then the secondary hydroxy group is converted with an alkanesulfonylation agent.

When the leaving group X is an arenesulfonyloxy group, the primary hydroxy group of (1RS,2SR)-(2-hydroxy-3,5,5-trimethyl-3-cyclopentenyl)methanol (5C) is esterified, and the secondary hydroxy group is converted with an arenesulfonylation agent.

[4] Step A

A process for preparing (2-hydroxy-3,5,5-trimethyl-3-cyclopentenyl)methanol (5) will be described below. (2-Hydroxy-3,5,5-trimethyl-3-cyclopentenyl)methanol (5) is synthesized by subjecting the 3,5,5-trimethyl-2-oxo-3-cyclopentene-1-carboxylate ester compound (6) (hereinafter also referred to as starting material (6)) to a reduction reaction.

The preparation process may be any one out of: (i) process for directly reducing the starting material (6), and (ii) process for converting the starting material (6) to its corresponding carboxylic acid and subjecting the carboxylic acid to a reduction reaction.

First, (i) process for directly reducing the starting material (6) will be explained.

(2-Hydroxy-3,5,5-trimethyl-3-cyclopentenyl)methanol (5) is synthesized by subjecting the 3,5,5-trimethyl-2-oxo-3-cyclopentene-1-carboxylate ester compound (6) to a reduction reaction, as shown in the following chemical reaction formula.

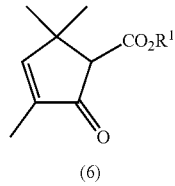 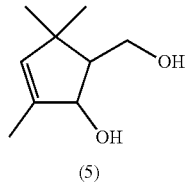

$R^1$ in the general formula (6) represents a monovalent hydrocarbon group having 1 to 10, preferably 1 to 6 carbon atoms.

Examples of the monovalent hydrocarbon group, $R^1$, include linear saturated hydrocarbon groups such as a methyl group, an ethyl group, an n-propyl group, an n-butyl group, an n-pentyl group, an n-hexyl group, an n-heptyl group, an n-octyl group, an n-nonyl group, and an n-decyl group; branched saturated hydrocarbon groups such as an isopropyl group, a 2-methylbutyl group, and a t-butyl group; cyclic, saturated hydrocarbon groups such as a cyclopropyl group, a cyclobutyl group, a cyclopentyl group, a cyclohexyl group, and a cyclopentylmethyl group; linear unsaturated hydrocarbon groups such as a vinyl group, an allyl group, and an ethynyl group; branched unsaturated hydrocarbon groups such as an isopropenyl group and a 2-methyl-2-propenyl group; cyclic unsaturated hydrocarbon groups such as a phenyl group, a tolyl group, a dimethylphenyl group, a benzyl group, and a phenethyl group; and isomers thereof. A part of the hydrogen atoms in the hydrocarbon groups may be substituted with a monovalent hydrocarbon group having 1 to 9 carbon atoms.

Specific examples of the 3,5,5-trimethyl-2-oxo-3-cyclopentene-1-carboxylate ester compound (6) include ethyl 3,5,5-trimethyl-2-oxo-3-cyclopentene-1-carboxylate (6A), t-butyl 3,5,5-trimethyl-2-oxo-3-cyclopentene-1-carboxylate, and phenyl 3,5,5-trimethyl-2-oxo-3-cyclopentene-1-carboxylate.

(2-Hydroxy-3,5,5-trimethyl-3-cyclopentenyl)methanol (5) has four stereoisomers. That is, (2-hydroxy-3,5,5-trimethyl-3-cyclopentenyl)methanol (5) comprises (1R,2R)-(2-hydroxy-3,5,5-trimethyl-3-cyclopentenyl)methanol of the following formula (5-1), (1R,2S)-(2-hydroxy-3,5,5-trimethyl-3-cyclopentenyl)methanol of the following formula (5-2), (1S,2R)-(2-hydroxy-3,5,5-trimethyl-3-cyclopentenyl)methanol of the following formula (5-3), and (1S,2S)-(2-hydroxy-3,5,5-trimethyl-3-cyclopentenyl)methanol of the following formula (5-4), and racemates, scalemic mixtures, and diastereomeric mixtures thereof.

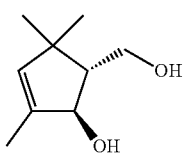

(5-1)

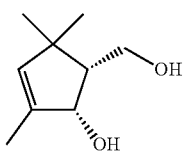

(5-2)

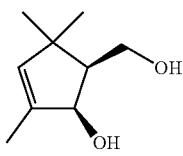

(5-3)

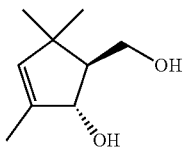

(5-4)

The hashed wedged bonds and the bold wedged bond in the general formula (5-1), (5-2, (5-3) and (5-4) represent absolute configurations.

The aforesaid (1RS,2SR)-(2-hydroxy-3,5,5-trimethyl-3-cyclopentenyl)methanol (5C) is, among the four stereoisomers, (5-1) to (5-4) of (2-hydroxy-3,5,5-trimethyl-3-cyclopentenyl)methanol, (1R,2 S)-(2-hydroxy-3,5,5-trimethyl-3-cyclopentenyl)methanol (5-2) and/or (1S,2R)-(2-hydroxy-3,5,5-trimethyl-3-cyclopentenyl)methanol (5-3), or both.

The reduction reaction may be done as in any known reduction reaction of a carboxylate ester. In the reduction reaction, the reaction substrate is reacted with a reducing agent in a solvent, if needed, with cooling or heating.

The reaction substrate depends on a reducing agent and/or a reaction conditions to be used. For instance, the 3,5,5-trimethyl-2-oxo-3-cyclopentene-1-carboxylate ester compound (6) may be used as such as a substrate for the reduction, when $R^1$ in the ester is a primary or secondary alkyl group.

Examples of the reducing agent used in the reduction reaction include hydrogen; boron compounds such as borane, alkylborane, dialkylborane, and bis(3-methyl-2-butyl)borane; metal hydrides such as dialkylsilane, trialkylsilane, monoalkylaluminum hydride, and dialkylaluminum hydride; complex hydrides such as sodium borohydride, lithium borohydride, potassium borohydride, calcium borohydride, sodium aluminum hydride, lithium aluminum hydride, sodium trimethoxy borohydride, zinc borohydride, lithium trimethoxy aluminum hydride, lithium diethoxy aluminum hydride, lithium tri-t-butoxy aluminum hydride, sodium bis(2-methoxyethoxy) aluminum hydride, lithium triethyl borohydride, and diisobutylaluminum hydride; and alkoxy derivatives or alkyl derivatives thereof. The complex hydrides are preferred in view of reaction conditions and/or ease of the work-up process.

An amount of the reducing agent used in the reduction reaction varies, depending on a reducing agent and/or reaction conditions to be used, and is preferably from 0.5 to 500 mol, more preferably 0.9 to 8 mol, per mol of the substrate, i.e., the 3,5,5-trimethyl-2-oxo-3-cyclopentene-1-carboxylate ester compound (6).

Examples of a solvent used in the reduction reaction include water; alcohol solvents such as methanol, ethanol, isopropyl alcohol, t-butyl alcohol, benzyl alcohol, methoxyethanol, and ethoxy ethanol; ether solvents such as ethylene glycol monomethyl ether, triethylene glycol monomethyl ether, tetrahydrofuran, 4-methyltetrahydropyran, diethyl ether, t-butyl methyl ether, and 1,4-dioxane; hydrocarbon solvents such as toluene, xylene, and hexane; and polar solvents such as N,N-dimethylformamide, N,N-dimethylacetamide, acetonitrile, dichloromethane, and chloroform.

The solvent may be used either alone or in combination thereof, if necessary. The solvent may be commercially available one.

The solvent used in the reduction reaction is appropriately selected, depending on a reducing agent to be used. Examples of a preferred combination of a reducing agent and a solvent include a combination of a reducing agent, lithium borohydride, with an ether solvent, a mixed solvent of an ether solvent and an alcohol solvent, or a mixed solvent of an ether solvent and a hydrocarbon solvent; and a combination of a reducing agent, lithium aluminum hydride, with an ether solvent or a mixed solvent of an ether solvent and a hydrocarbon solvent.

An amount of the solvent used in the reduction reaction varies, depending on a production scale, and is preferably from 0.01 to 100,000 g, more preferably 0.1 to 10,000 g, even more preferably 1 to 1,000 g, per mol of the substrate (6) in view of the reaction rate.

A reaction temperature of the reduction reaction is preferably from −78 to 100° C., more preferably −20 to 80° C., in view of the reaction rate and suppression of by-product formation.

A reaction time of the reduction reaction varies, depending on a solvent used and/or a production scale, and is preferably from 0.1 to 120 hours.

Specific examples of the process for preparing (2-hydroxy-3,5,5-trimethyl-3-cyclopentenyl)methanol (5) include a process of reacting ethyl 3,5,5-trimethyl-2-oxo-3-cyclopentene-1-carboxylate (6A) with lithium aluminum hydride, as shown in the following chemical reaction formula.

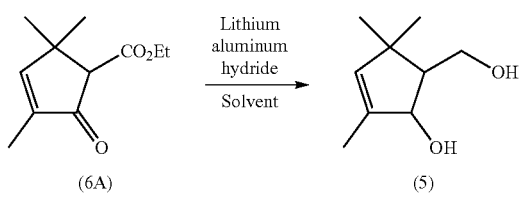

(1RS,2SR)-(2-hydroxy-3,5,5-trimethyl-3-cyclopentenyl) methanol (5C) among (2-hydroxy-3,5,5-trimethyl-3-cyclopentenyl)methanol (5) is synthesized by subjecting 3,5,5-trimethyl-2-oxo-3-cyclopentene-1-carboxylate ester compound (6) directly to a reduction reaction, like the case of (2-hydroxy-3,5,5-trimethyl-3-cyclopentenyl)methanol (5).

Next, step A to obtain (1RS,2SR)-(2-hydroxy-3,5,5-trimethyl-3-cyclopentenyl)methanol (5C) will be explained.

Depending upon a solvent and/or reducing agent to be used, the stereoisomer ratio of (2-hydroxy-3,5,5-trimethyl-3-cyclopentenyl)methanol (5) may vary, so that (1RS,2SR)-(2-hydroxy-3,5,5-trimethyl-3-cyclopentenyl)methanol (5C) may be selectively prepared. The solvent and the reducing agent may be those mentioned for the reduction reaction. A person skilled in the art can select a solvent suitable for a stereoselective reaction from the solvents described above. The stereoselective reaction may proceed, using, for example, a Lewis-acidic reducing agent, for example, diisobutylaluminum hydride.

An examples of the process for preparing (1RS,2SR)-(2-hydroxy-3,5,5-trimethyl-3-cyclopentenyl)methanol (5C) is a process for reacting ethyl 3,5,5-trimethyl-2-oxo-3-cyclopentene-1-carboxylate (6A) with diisobutylaluminum hydride, as shown in the following chemical reaction formula.

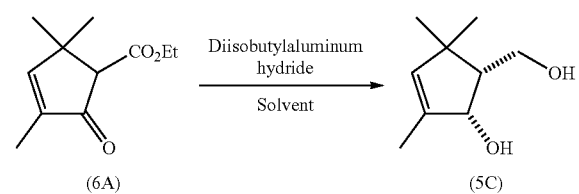

Next, the aforesaid process (ii) will be explained, where the starting material (6) is converted into its corresponding carboxylic acid, which is then reduced.

(2-Hydroxy-3,5,5-trimethyl-3-cyclopentenyl)methanol (5) is synthesized by converting the 3,5,5-trimethyl-2-oxo-3-cyclopentene-1-carboxylate ester compound (6) into its corresponding carboxylic acid, 3,5,5-trimethyl-2-oxo-3-cyclopentene-1-carboxylic acid, which is then subjected to a reduction reaction.

First, the conversion of the 3,5,5-trimethyl-2-oxo-3-cyclopentene-1-carboxylate ester compound (6) into 3,5,5-trimethyl-2-oxo-3-cyclopentene-1-carboxylic acid will be described.

The conversion of the 3,5,5-trimethyl-2-oxo-3-cyclopentene-1-carboxylate ester compound (6) into 3,5,5-trimethyl-2-oxo-3-cyclopentene-1-carboxylic acid may be done as in any known conversion reaction from an ester to a carboxylic acid, such as a hydrolysis reaction in a basic or neutral condition, or elimination reaction in an acidic condition. The hydrolysis reaction is preferred in a case where $R^1$ in the substrate ester compound (6) is a primary or secondary alkyl group. The elimination reaction is preferred when $R^1$ is a tertiary alkyl group.

In the hydrolysis reaction, the reaction substrate is reacted with water in a solvent or water added, usually in the presence of a base or salt. In the elimination reaction, the reaction is promoted with an acid in a solvent. In the both reactions, cooling or heating may be conducted, if necessary.

Examples of the base used in the hydrolysis reaction include hydroxides such as sodium hydroxide, lithium hydroxide, potassium hydroxide, and barium hydroxide; carbonate salts such as sodium carbonate, potassium carbonate, sodium bicarbonate, and potassium bicarbonate; and metal alkoxides such as sodium methoxide, sodium ethoxide, sodium t-butoxide, sodium t-amiloxide, lithium methoxide, lithium ethoxide, lithium t-butoxide, lithium t-amiloxide, potassium methoxide, potassium ethoxide, potassium t-butoxide, and potassium t-amiloxide.

The base may be used either alone or in combination thereof, if necessary. The base may be commercially available one.

An amount of the base used is preferably from 1 to 1,000 mol, more preferably 1 to 100 mol, even more preferably 1 to 10 mol, per mol of the 3,5,5-trimethyl-2-oxo-3-cyclopentene-1-carboxylate ester compound (6) in view of the reactivity.

Examples of the salts used in the hydrolysis include salts of inorganic acids such as salts of hydrochloric acid, hydrobromic acid, hydroiodic acid, sulfuric acid, nitric acid, boric acid, and phosphoric acid; salts of organic acids such as salts of formic acid, acetic acid, propionic acid, oxalic acid, trifluoroacetic acid, methanesulfonic acid, benzenesulfonic acid, p-toluenesulfonic acid, and naphthalenesulfonic acid; Lewis acids such as aluminum trichloride, aluminum ethoxide, aluminum isopropoxide, aluminum oxide, boron trifluoride, boron trichloride, boron tribromide, tin tetrachloride, tin tetrabromide, dibutyltin dichloride, dibutyltin dimethoxide, dibutyltin oxide, titanium tetrachloride, titanium tetrabromide, titanium (IV) methoxide, titanium (IV) ethoxide, titanium (IV) isopropoxide, and titanium (IV) oxide; and oxides such as alumina, silica gel, and titania.

The salt may be used either alone or in combination thereof, if necessary. The salts may be commercially available one.

An amount of the salt used is preferably from 1 to 1,000 mol, more preferably 1 to 100 mol, even more preferably 1 to 10 mol, per mol of the 3,5,5-trimethyl-2-oxo-3-cyclopentene-1-carboxylate ester compound (6) in view of the reactivity.

Examples of the acid used in the elimination reaction include inorganic acids such as hydrochloric acid, hydrobromic acid, hydroiodic acid, sulfuric acid, nitric acid, boric acid, and phosphoric acid; organic acids such as formic acid, acetic acid, propionic acid, oxalic acid, trifluoroacetic acid, methanesulfonic acid, benzenesulfonic acid, p-toluenesulfonic acid, and naphthalenesulfonic acid; and Lewis acids such as aluminum trichloride, aluminum ethoxide, aluminum isopropoxide, aluminum oxide, boron trifluoride, boron trichloride, boron tribromide, tin tetrachloride, tin tetrabromide, dibutyltin dichloride, dibutyltin dimethoxide, dibutyltin oxide, titanium tetrachloride, titanium tetrabromide, titanium (IV) methoxide, titanium (IV) ethoxide, titanium (IV) isopropoxide, and titanium (IV) oxide.

The acid may be used either alone or in combination thereof, if necessary. The acid may be commercially available one.

An amount of the acid used is preferably 0.0001 to 1,000 mol, more preferably 0.001 to 100 mol, even more preferably 0.01 to 10 mol, per mol of the 3,5,5-trimethyl-2-oxo-3-cyclopentene-1-carboxylate ester compound (6) in view of the reactivity.

Examples of the solvent used in the hydrolysis reaction or elimination reaction include water; alcohol solvents such as methanol, ethanol, isopropyl alcohol, t-butyl alcohol, benzyl alcohol, methoxyethanol, and ethoxy ethanol; ether solvents such as ethylene glycol monomethyl ether, triethylene glycol monomethyl ether, tetrahydrofuran, 4-methyltetrahydropyran, diethyl ether, t-butyl methyl ether, and 1,4-dioxane; hydrocarbon solvents such as toluene, xylene, and hexane; and polar solvents such as N,N-dimethylformamide, N,N-dimethylacetamide, acetonitrile, dichloromethane, and chloroform.

The solvent may be used either alone or in combination thereof, if necessary. The solvent may be commercially available one.

An amount of the solvent used varies, depending on a production scale, and is preferably 0.01 to 200,000 g, more preferably 0.1 to 20,000 g, even more preferably 1 to 2,000 g, per mol of the 3,5,5-trimethyl-2-oxo-3-cyclopentene-1-carboxylate ester compound (6) in view of the reaction rate.

A reaction temperature in the hydrolysis reaction or elimination reaction is preferably from −78° C. to a boiling point temperature of a solvent, and more preferably −10 to 100° C., in view of the reaction rate and suppression of by-product formation.

A reaction time of the hydrolysis reaction or elimination reaction varies, depending on a solvent and/or a reaction scale to be used, and is preferably from 0.1 to 120 hours.

Next, the reduction reaction of 3,5,5-trimethyl-2-oxo-3-cyclopentene-1-carboxylic acid will be explained.

The reduction reaction may be done as in any known reduction reaction from a carboxylic acid to an alcohol. The reduction reaction is typically performed by reacting a reaction substrate with a reducing agent usually in a solvent, with cooling or heating if needed.

For instance, when $R^1$ is a tertiary group causing severe steric hindrance, the reduction reaction is likely to proceed slowly, though depending on a reducing agent and/or reaction conditions to be used. Accordingly, it is preferred to convert the 3, 5, 5-trimethyl-2-oxo-3-cyclopentene-1-carboxylate ester compound (6) into 3,5,5-trimethyl-2-oxo-3-cyclopentene-1-carboxylic acid, which is used as a reaction substrate of the reduction reaction.

The reducing agent, an amount of the reducing agent, the solvent, an amount of the solvent, and the reaction temperature and reaction time in the reduction reaction are as mentioned above.

Another specific example of the process for preparing (1RS,2SR)-(2-hydroxy-3,5,5-trimethyl-3-cyclopentenyl)

methanol (5C) comprises converting the 3,5,5-trimethyl-2-oxo-3-cyclopentene-1-carboxylate ester compound (6) into its corresponding 3,5,5-trimethyl-2-oxo-3-cyclopentene-1-carboxylic acid and subjecting this carboxylic acid to a reduction reaction. Also in this reduction method, for example, diisobutylaluminum hydride may be used as a reducing agent.

EXAMPLES

The present invention will be described with reference to the following Examples. It should be construed that the present invention is not limited to or by the Examples.

The term "purity" as used herein means an area percentage determined by gas chromatography (hereinafter referred to also as "GC"), unless otherwise specified. The term "production ratio" means a relative ratio of area percentages determined by GC.

A yield is calculated from the area percentages determined by GC.

The yield was calculated by the following equation in consideration of purities (% GC) of a starting material and a product.

Yield(%)=[(mass of a product obtained in a reaction×% GC)/molecular mass of a product]÷
[(mass of a starting material×% GC)/molecular mass of a starting material]}×100

The term "crude yield" refers to a yield of a crude product obtained without purification.

In the Examples, monitoring of the reactions and calculation of the yields were carried out in the following GC conditions.

GC conditions: GC: Capillary gas chromatograph GC-2014 (Shimadzu Corporation); column: DB-5, 0.25 um×0.25 mmϕ×30 m; carrier gas: He (1.55 mL/min), detector: FID; column temperature: 100° C., elevated by 10° C./min, up to 230° C.

Example 1: Preparation of (1RS,4RS)-(3,4,5,5-tetramethyl-2-cyclopentenyl)methyl isobutyrate (3A)

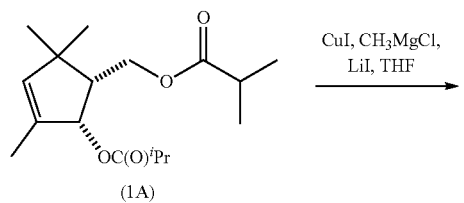

wherein $^i$Pr represents an isopropyl group.

Copper (I) iodide (85.7 g, 0.450 mol) and tetrahydrofuran (THF) (801 g) were placed in a reactor and cooled to a range of 0 to 4° C. Lithium iodide (121 g, 0.904 mol) was then added at or below 10° C. Subsequently, a 0.00258 mol/g solution of methylmagnesium chloride in THF (348 g, 0.898 mol) was added dropwise at or below 10° C. After the completion of the dropwise addition, the resulting reaction mixture was stirred at 0 to 4° C. for 30 minutes to prepare a solution of a methylating agent in THF.

Next, (1RS,2SR)-(3,5,5-trimethyl-2-isobutyryloxy-3-cyclopentenyl)methyl isobutyrate (1A) (88.9 g, 0.300 mol) and THF (91.2 g) were placed in another reaction vessel and stirred at 37 to 42° C. for 30 minutes. The aforesaid solution of the methylating agent in THF was then added dropwise at 35 to 45° C. After the completion of the dropwise addition, the reaction mixture was stirred at 37 to 42° C. for 3.5 hours. After the completion of the stirring, the reaction mixture was cooled to 4 to 10° C., and an aqueous solution of ammonium chloride (354 g: prepared from ammonium chloride (32 g) and water (322 g)) was added to quench the reaction. Further, 20 wt % hydrochloric acid (64.4 g) and hexane (1,200 g) were added to the resulting reaction mixture, and the reaction mixture was phase-separated. The organic layer was washed with aqueous ammonia (1,781 g: prepared from ammonium chloride (58 g), aqueous 25 wt % sodium hydroxide solution (193 g), and water (1,530 g)) four times. The washed organic layer was further washed with brine (1,589 g: prepared from sodium chloride (59 g) and water (1,530 g)). The resulting organic layer was concentrated at a reduced pressure, and the concentrate was distilled at a reduced pressure to obtain the target compound, (1RS,4RS)-(3,4,5,5-tetramethyl-2-cyclopentenyl)methyl isobutyrate (3A) (65.5 g, 0.292 mol) in 97.3% yield.

The following are spectrum data of the obtained (1RS,4RS)-(3,4,5,5-tetramethyl-2-cyclopentenyl)methyl isobutyrate (3A).

Nuclear magnetic resonance spectrum: $^1$H-NMR (500 MHz, CDCl$_3$): δ=0.88 (d, J=7.3 Hz, 3H), 0.95 (s, 3H), 0.96 (s, 3H), 1.16 (d, J=6.9 Hz, 6H), 1.65 (q, J=1.9 Hz, 3H), 2.10-2.15 (m, 1H), 2.45-2.49 (m, 1H), 2.49-2.56 (m, 1H), 3.93 (dd, J=11.1, 6.9 Hz, 1H), 4.10 (dd, J=11.1, 6.5 Hz, 1H), 5.14-5.15 (m, 1H); $^{13}$C-NMR (75.6 MHz, CDCl$_3$): δ=12.36, 15.17, 18.97, 19.00, 23.95, 24.59, 34.13, 43.01, 52.52, 52.61, 64.59, 123.03, 145.27, 177.21.

GC-MS (EI, 70 eV): m/z 224 (M$^+$), 136, 121, 105, 93, 81, 67, 55, 43, 27.

Infrared absorption spectrum (NaCl): νmax 3040, 2966, 2873, 1737, 1470, 1387, 1258, 1191, 1157, 1074, 982, 919, 826, 755.

Example 2: Preparation of (1RS)-(2,2,3,4-tetramethyl-3-cyclopentenyl)methyl isobutyrate (4A)

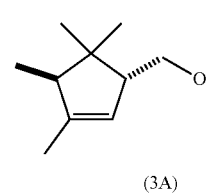

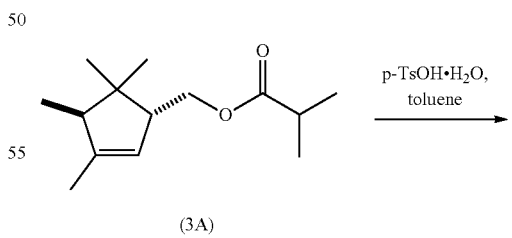

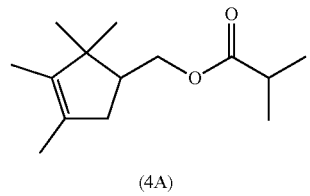

(1RS,4RS)-(3,4,5,5-tetramethyl-2-cyclopentenyl)methyl isobutyrate (3A) obtained in Example 1 (0.61 g, 2.7 mmol), p-toluenesulfonic acid monohydrate (p-TsOH.H$_2$O) (0.08 g, 0.4 mmol), and toluene (20 mL) were placed in a reactor and stirred at 100 to 110° C. for 9 hours. The reaction mixture was then cooled to 4 to 10° C., and an aqueous solution of sodium bicarbonate (10.1 g: prepared from sodium bicarbonate (0.10 g) and water (10 g)) was added to quench the reaction. The resulting reaction mixture was phase-separated, and the organic layer was washed with saturated brine (30 mL). The resulting organic layer was concentrated at a reduced pressure, and the concentrate was purified by silica gel column chromatography (eluent: a gradient of n-hexane: ethyl acetate=100:1 to 80:1) to obtain the target compound, (1RS)-(2,2,3,4-tetramethyl-3-cyclopentenyl)methyl isobutyrate (4A) (0.55 g, 2.4 mmol) in 89% yield.

The following are spectrum data of the (1RS)-(2,2,3,4-tetramethyl-3-cyclopentenyl)methyl isobutyrate (4A) thus prepared.

Nuclear magnetic resonance spectrum: $^1$H-NMR (500 MHz, CDCl$_3$): δ=0.82 (s, 3H), 1.05 (s, 3H), 1.168 (d, J=6.9 Hz, 3H), 1.169 (d, J=6.9 Hz, 3H), 1.47-1.48 (m, 3H), 1.58 (brd, J=1.2 Hz, 3H), 1.95-2.01 (m, 1H), 2.09-2.15 (m, 1H), 2.21-2.26 (m, 1H), 2.50-2.58 (m, 1H), 4.09 (dd, J=11.1, 7.7 Hz, 1H), 4.15 (dd, J=11.1, 6.9 Hz, 1H); $^{13}$C-NMR (75.6 MHz, CDCl$_3$): δ=9.20, 14.09, 18.99, 19.02, 19.92, 27.01, 34.12, 39.06, 46.74, 47.67, 65.62, 127.85, 138.52, 177.27.

GC-MS (EI, 70 eV): m/z 224 (M$^+$), 136, 121, 105, 93, 79, 67, 55, 43, 27.

Infrared absorption spectrum (NaCl): vmax 2967, 2929, 1737, 1470, 1386, 1360, 1261, 1193, 1157, 1073, 979, 919.

Example 3: Preparation of (1RS,2SR)-(2-hydroxy-3,5,5-trimethyl-3-cyclopentenyl)methanol (5C)

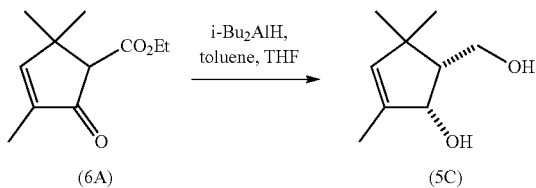

wherein Et represents an ethyl group and i-Bu represents an isobutyl group.

Ethyl 3,5,5-trimethyl-2-oxo-3-cyclopentene-1-carboxylate (6A) (84.1 g, 0.429 mol) and THF (1,029 g) were placed in a reactor and stirred at −5 to 5° C. for 30 minutes. A 1.0 mol/L solution of diisobutylaluminum hydride (i-Bu$_2$AlH) in toluene (1,500 mL, 1.50 mol) was then added dropwise to the mixture at −5 to 5° C. After the completion of the dropwise addition, the reaction mixture was stirred at room temperature for 30 minutes and further at 55° C. for 2 hours. After the completion of the stirring, the reaction mixture was cooled to 4 to 10° C., and ethanol (108 g, 2.34 mol) was added to quench the reaction. Further, a saturated aqueous solution of potassium sodium tartrate (1,500 mL) was added dropwise. After the completion of the dropwise addition, the mixture was stirred at room temperature for 15 hours and further at 50° C. for 2 hours. After the completion of the stirring, the resulting reaction mixture was phase-separated. The organic layer was washed with saturated brine (1,000 mL), and the resulting organic layer was concentrated at a reduced pressure to obtain crude crystals. The resulting crude crystals were recrystallized in n-hexane (500 mL) and ethyl acetate (78.5 mL) to obtain the target compound, (1RS,2SR)-(2-hydroxy-3,5,5-trimethyl-3-cyclopentenyl)methanol (5C) (24.6 g, 0.158 mol) in 36.8% yield.

The following are spectrum data of the (1RS,2SR)-(2-hydroxy-3,5,5-trimethyl-3-cyclopentenyl)methanol (5C) thus prepared.

Nuclear magnetic resonance spectrum: $^1$H-NMR (500 MHz, CDCl$_3$): δ=0.97 (s, 3H), 1.06 (s, 3H), 1.77-1.78 (m, 3H), 2.05 (ddd, J=10.0, 6.5, 5.4 Hz, 1H), 3.79 (dd, J=10.7, 5.4 Hz, 1H), 3.95 (dd, J=10.7, 10.0 Hz, 1H), 4.58 (d, J=6.5 Hz, 1H), 5.39 (q, J=1.5 Hz, 1H); $^{13}$C-NMR (75.6 MHz, CDCl$_3$): δ=13.96, 25.45, 28.92, 44.67, 54.14, 59.86, 80.37, 137.91, 140.81.

GC-MS (EI, 70 eV): m/z 156 (M$^+$), 141, 125, 109, 95, 77, 67, 55, 43, 29.

Infrared absorption spectrum (NaCl): vmax 3312, 3021, 2971, 2946, 2862, 1443, 1404, 1215, 1112, 1091, 1030, 971, 952, 902, 873, 772, 718, 644, 594.

Example 4: Preparation of (2-hydroxy-3,5,5-trimethyl-3-cyclopentenyl)methanol (5)

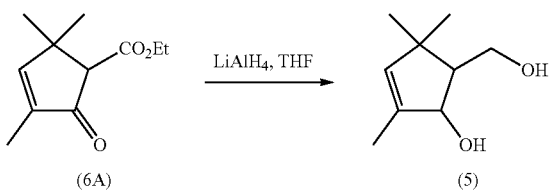

wherein Et represents an ethyl group.

Lithium aluminum hydride (0.57 g, 15 mmol) and THF (18.7 g) were placed in a reactor and stirred at room temperature for 1.5 hours. The reaction mixture was then cooled to 4 to 10° C., and ethyl 3,5,5-trimethyl-2-oxo-3-cyclopentene-1-carboxylate (6A) (1.43 g, 7.27 mmol) and THF (1.00 g) were added dropwise at 4 to 12° C. After the completion of the dropwise addition, the reaction mixture was stirred at 20 to 25° C. for 2 hours. Subsequently, the reaction mixture was cooled to 4 to 10° C., and water (1.13 g), aqueous 25 wt % sodium hydroxide solution (0.66 g), and water (3.89 g) were sequentially added to quench the reaction. Next, the reaction mixture was filtered through Celite, and the resulting filtrate was concentrated at a reduced pressure. The concentrate was purified by silica gel column chromatography (eluent: a gradient of n-hexane: ethyl acetate=20:1 to 2:3) to obtain the target compound, (2-hydroxy-3,5,5-trimethyl-3-cyclopentenyl)methanol (5) (0.41 g, 2.6 mmol) as a 45:55 mixture of (1RS,2SR)-(2-hydroxy-3,5,5-trimethyl-3-cyclopentenyl)methanol (5C) and (1RS,2RS)-(2-hydroxy-3,5,5-trimethyl-3-cyclopentenyl)methanol in 36% yield.

The spectrum data of the (1RS,2SR)-(2-hydroxy-3,5,5-trimethyl-3-cyclopentenyl)methanol (5C) thus prepared were the same as those determined in Example 3.

The following are spectrum data of the (1RS,2RS)-(2-hydroxy-3,5,5-trimethyl-3-cyclopentenyl)methanol thus prepared.

Nuclear magnetic resonance spectrum: $^1$H-NMR (500 MHz, CDCl$_3$): δ=0.84 (s, 3H), 1.12 (s, 3H), 1.70-1.71 (m, 3H), 1.88 (ddd, J=10.0, 7.6, 5.4 Hz, 1H), 3.83 (dd, J=10.0, 10.0 Hz, 1H), 3.90 (dd, J=10.0, 5.4 Hz, 1H), 4.50 (d, J=7.6

Hz, 1H), 5.28 (q, J=1.5 Hz, 1H); $^{13}$C-NMR (75.6 MHz, CDCl$_3$): δ=13.04, 23.47, 29.20, 43.04, 60.13, 60.21, 83.39, 137.47, 138.45.

GC-MS (EI, 70 eV): m/z 156 (M$^+$), 141, 125, 109, 95, 77, 67, 55, 43, 29. Infrared absorption spectrum (NaCl): vmax 3335, 3022, 2954, 2866, 1463, 1448, 1361, 1254, 1152, 1090, 1043, 999, 947, 883, 830, 627.

Example 5: Preparation of (1RS,2SR)-(3,5,5-trimethyl-2-isobutyryloxy-3-cyclopentenyl)methyl isobutyrate (1A)

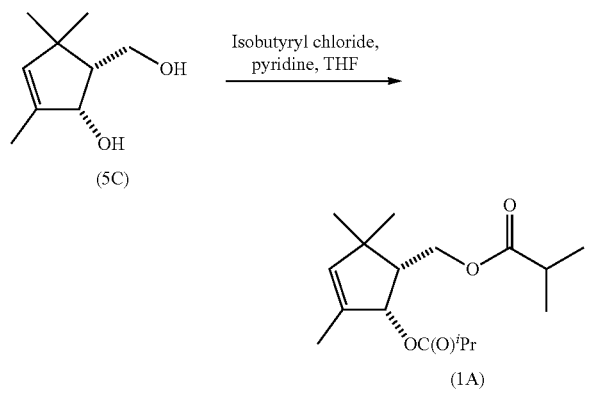

wherein $^i$Pr represents an isopropyl group.

(1RS,2SR)-(2-hydroxy-3,5,5-trimethyl-3-cyclopentenyl)methanol (5C) prepared according to the procedures described in Example 3 (137 g, 0.876 mol), THF (435 g), and pyridine (249 g, 3.15 mol) were placed in a reactor and stirred at 4 to 10° C. for 1 hour. Isobutyryl chloride (215 g, 2.01 mol) was then added dropwise to the mixture at or below 15° C. After the completion of the dropwise addition, the reaction mixture was stirred at 4 to 10° C. for 3 hours, and brine (2,882 g: sodium chloride (262 g) and water (2,620 g)) was added to quench the reaction. Subsequently, hexane (545 g) was added to the reaction mixture, and the resulting mixture was phase-separated. The organic layer was washed with hydrochloric acid (2,804 g: prepared from 20 wt % hydrochloric acid (117 g), sodium chloride (65 g), and water (2,622 g)). Further, the organic layer was washed sequentially with brine (2,687 g: prepared from sodium chloride (65 g) and water (2,622 g)), an aqueous solution of sodium carbonate (2,753 g: prepared from sodium carbonate (131 g) and water (2,622 g)), and brine (2,882 g: prepared from sodium chloride (262 g) and water (2,620 g)). The resulting organic layer was concentrated at a reduced pressure, and the concentrate was distilled at a reduced pressure to obtain the target compound, (1RS,2SR)-(3,5,5-trimethyl-2-isobutyryloxy-3-cyclopentenyl)methyl isobutyrate (1A) (255 g, 0.860 mol) in 98.2% yield.

The following are spectrum data of the (1RS,2SR)-(3,5,5-trimethyl-2-isobutyryloxy-3-cyclopentenyl)methyl isobutyrate (1A) thus prepared. Nuclear magnetic resonance spectrum: $^1$H-NMR (500 MHz, CDCl$_3$): δ 1.00 (s, 3H), 1.12 (s, 3H), 1.12-1.15 (m, 12H), 1.65 (d, J=1.5 Hz, 3H), 2.28 (ddd, J=9.2, 6.5, 6.5 Hz, 1H), 2.48-2.54 (m, 2H), 4.11 (dd, J=11.1, 6.5 Hz, 1H), 4.17 (dd, J=11.1, 9.2 Hz, 1H), 5.49 (q, J=1.5 Hz, 1H), 5.70 (d, J=6.5 Hz, 1H); $^{13}$C-NMR (75.6 MHz, CDCl$_3$): δ 14.30, 18.89, 18.94, 19.04 (2C), 24.48, 27.84, 33.98, 34.28, 45.21, 50.19, 60.69, 79.97, 135.32, 143.10, 176.51, 177.07.

LC-MS (ESI, positive): m/z 314 (M$^+$+18).

Infrared absorption spectrum (NaCl): vmax 2972, 2874, 1734, 1471, 1386, 1256, 1192, 1157, 1115, 1087, 983, 961, 900, 850, 756.

The invention claimed is:

1. A process for preparing an α-necrodyl compound of the following general formula (3):

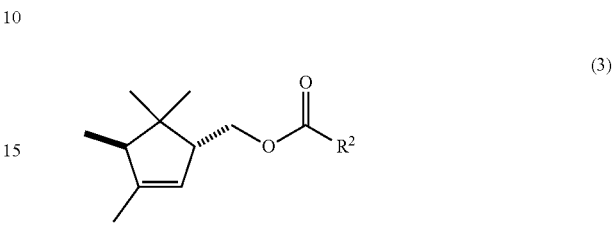

wherein R$^2$ represents a monovalent hydrocarbon group having 1 to 9 carbon atoms, and a bold unwedged bond and a hashed unwedged bond represent a relative configuration, the process comprising:
subjecting a 3, 5, 5-trimethyl-3-cyclopentene compound of the following general formula (1):

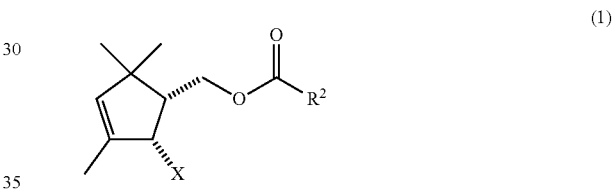

wherein R$^2$ is as defined above, X represents a leaving group, and hashed unwedged bonds represent a relative configuration, to a nucleophilic substitution reaction with a methylating agent of the following general formula (2):

$$CH_3\text{-}M \quad (2)$$

wherein M represents Li, MgZ$^1$, ZnZ$^1$, Cu, CuZ$^1$, or CuLiZ$^1$, and Z$^1$ represents a halogen atom or a methyl group, to form the α-necrodyl compound (3).

2. The process for preparing the α-necrodyl compound (3) according to claim 1, wherein the 3,5,5-trimethyl-3-cyclopentene compound (1) is (1RS, 2SR)-(3, 5, 5-trimethyl-2-isobutyryloxy-3-cyclopentenyl)methyl isobutyrate of the following formula (1A):

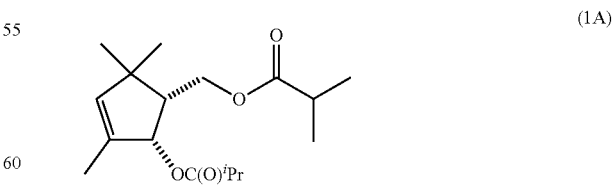

wherein $^i$Pr represents an isopropyl group, and hashed unwedged bonds represent a relative configuration, and the α-necrodyl compound (3) is (1RS, 4RS)-(3, 4, 5, 5-tetramethyl-2-cyclopentenyl)methyl isobutyrate of the following formula (3A):

(3A)

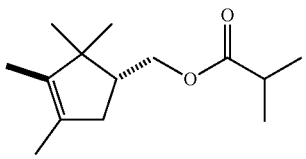

wherein the bold unwedged bond and the hashed unwedged bond represent a relative configuration.

3. A process for preparing a γ-necrodyl compound of the following general formula (4):

(4)

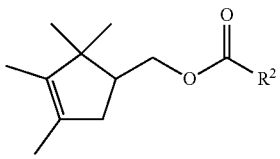

wherein $R^2$ represents a monovalent hydrocarbon group having 1 to 9 carbon atoms,
the process comprising:
  the process for preparing the α-necrodyl compound (3) according to claim 1, and
  subjecting the α-necrodyl compound (3) thus obtained to a positional isomerization reaction at the double bond to form the γ-necrodyl compound (4).

4. The process for preparing the γ-necrodyl compound (4) according to claim 3,
  wherein the γ-necrodyl compound (4) is (1RS)-(2, 2, 3, 4-tetramethyl-3-cyclopentenyl)methyl isobutyrate of the following formula (4A):

(4A)

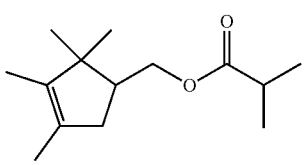

5. The process for preparing the α-necrodyl compound (3) according to claim 1, the process further comprising:
  subjecting (1RS,2SR)-(2-hydroxy-3, 5, 5-trimethyl-3-cyclopentenyl)methanol of the following formula (5C):

(5C)

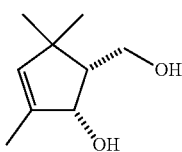

wherein hashed unwedged bonds represent a relative configuration,
to an esterification reaction, a combination of an esterification reaction with a halogenation reaction, or a combination of an esterification reaction with a sulfonylation reaction to form the 3,5,5-trimethyl-3-cyclopentene compound (1).

6. The process for preparing the α-necrodyl compound (3) according to claim 5, the process further comprising:
  subjecting a 3, 5, 5-trimethyl-2-oxo-3-cyclopentene-1-carboxylate ester compound of the following general formula (6):

(6)

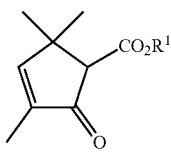

wherein $R^1$ represents a monovalent hydrocarbon group having 1 to 10 carbon atoms,
to a reduction reaction to form (1RS,2SR)-(2-hydroxy-3,5,5-trimethyl-3-cyclopentenyl)methanol (5C).

7. The process for preparing the α-necrodyl compound (3) according to claim 5, the process further comprising:
  converting a 3, 5, 5-trimethyl-2-oxo-3-cyclopentene-1-carboxylate ester compound of the following general formula (6):

(6)

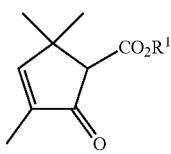

wherein $R^1$ represents a monovalent hydrocarbon group having 1 to 10 carbon atoms, into a corresponding carboxylic acid, and
  subjecting the carboxylic acid thus obtained to a reduction reaction to form (1RS,2SR)-(2-hydroxy-3,5,5-trimethyl-3-cyclopentenyl)methanol (5C).

8. A process for preparing a γ-necrodyl compound of the following general formula (4):

(4)

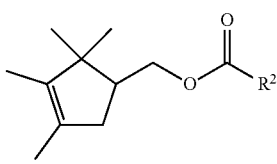

wherein $R^2$ represents a monovalent hydrocarbon group having 1 to 9 carbon atoms,
the process comprising:
  the process for preparing the α-necrodyl compound (3) according to claim 5, and
    subjecting the α-necrodyl compound (3) thus obtained to a positional isomerization reaction at the double bond to form the γ-necrodyl compound (4).

9. (2-Hydroxy-3, 5, 5-trimethyl-3-cyclopentenyl)methanol of the following formula (5):

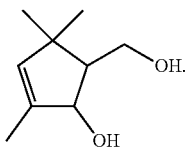

(5)

10. A process for preparing a γ-necrodyl compound of the following general formula (4):

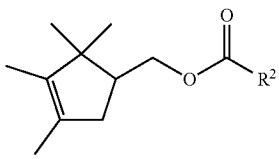

(4)

wherein $R^2$ represents a monovalent hydrocarbon group having 1 to 9 carbon atoms,
the process comprising:
  the process for preparing the α-necrodyl compound (3) according to claim 6, and
  subjecting the α-necrodyl compound (3) thus obtained to a positional isomerization reaction at the double bond to form the γ-necrodyl compound (4).

11. A process for preparing a γ-necrodyl compound of the following general formula (4):

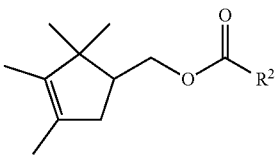

(4)

wherein $R^2$ represents a monovalent hydrocarbon group having 1 to 9 carbon atoms,
the process comprising:
  the process for preparing the α-necrodyl compound (3) according to claim 7, and
  subjecting the α-necrodyl compound (3) thus obtained to a positional isomerization reaction at the double bond to form the γ-necrodyl compound (4).

* * * * *

UNITED STATES PATENT AND TRADEMARK OFFICE
CERTIFICATE OF CORRECTION

PATENT NO. : 11,370,741 B2
APPLICATION NO. : 17/378952
DATED : June 28, 2022
INVENTOR(S) : Watanabe et al.

It is certified that error appears in the above-identified patent and that said Letters Patent is hereby corrected as shown below:

In the Specification

Column 17, Lines 40-46, Formula 3A-2: delete Formula 3A-2 and replace with the following:

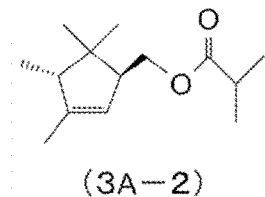

(3A-2)

Column 29, Line 25: delete "product]+" and insert --product]÷--

Column 31, Line 3: delete "(p-TsOH.H$_2$O)" and insert --(p-TsOH·H$_2$O)--

Signed and Sealed this
Ninth Day of May, 2023

Katherine Kelly Vidal
*Director of the United States Patent and Trademark Office*